US008335650B2

(12) United States Patent
Hsu et al.

(10) Patent No.: US 8,335,650 B2
(45) Date of Patent: Dec. 18, 2012

(54) METHODS AND APPARATUS TO DETERMINE PHASE-CHANGE PRESSURES

(75) Inventors: Kai Hsu, Sugar Land, TX (US); Kentaro Indo, Edmonton (CA); Peter S. Hegeman, Stafford, TX (US); Carsten Sonne, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 397 days.

(21) Appl. No.: 12/582,243

(22) Filed: Oct. 20, 2009

(65) Prior Publication Data

US 2011/0093200 A1 Apr. 21, 2011

(51) Int. Cl.
*G01V 5/04* (2006.01)

(52) U.S. Cl. ........ 702/8; 702/12; 73/152.18; 73/152.51; 73/152.55; 73/64.45; 166/263; 166/264; 166/252.1; 166/66.6; 324/636; 324/303

(58) Field of Classification Search ................ 702/8, 12; 73/152.18, 152.23, 864.63, 19.05, 61.47, 73/64.52; 166/264, 250.01, 309, 165
See application file for complete search history.

(56) References Cited

U.S. PATENT DOCUMENTS

| | | | |
|---|---|---|---|
| 4,782,695 A | 11/1988 | Glotin et al. | |
| 5,167,149 A | 12/1992 | Mullins et al. | |
| 5,329,811 A | 7/1994 | Schultz et al. | |
| 5,473,939 A | 12/1995 | Leder et al. | |
| 5,635,631 A | 6/1997 | Yesudas et al. | |
| 5,741,962 A | 4/1998 | Birchak et al. | |
| 6,128,949 A * | 10/2000 | Kleinberg | 73/152.18 |
| 6,223,588 B1 | 5/2001 | Burgass et al. | |
| 6,334,489 B1 | 1/2002 | Shwe et al. | |
| 6,439,307 B1 * | 8/2002 | Reinhardt | 166/264 |
| 6,490,916 B1 | 12/2002 | Goodwin et al. | |
| 6,501,072 B2 | 12/2002 | Mullins et al. | |
| 6,557,632 B2 * | 5/2003 | Cernosek | 166/264 |
| RE38,129 E * | 6/2003 | Kleinberg | 73/152.18 |
| 6,672,163 B2 | 1/2004 | Han et al. | |
| 6,758,090 B2 | 7/2004 | Bostrom et al. | |
| 6,792,798 B2 | 9/2004 | Liang | |
| 6,879,166 B2 * | 4/2005 | May et al. | 324/636 |
| 6,964,301 B2 | 11/2005 | Hill et al. | |
| 7,002,142 B2 | 2/2006 | Mullins et al. | |
| 7,075,063 B2 | 7/2006 | Dong et al. | |
| 7,114,562 B2 | 10/2006 | Fisseler et al. | |
| 7,216,533 B2 | 5/2007 | McGregor et al. | |
| 7,234,521 B2 | 6/2007 | Shammai et al. | |
| 7,346,460 B2 | 3/2008 | DiFoggio et al. | |

(Continued)

OTHER PUBLICATIONS

Lee et al, "Using PV Tests for Bubble Point Pressures and Quality Control," SPWLA 44th Annual Logging Symposium, Jun. 22-25, 2003, Paper HH.

(Continued)

*Primary Examiner* — Carol Tsai
(74) *Attorney, Agent, or Firm* — John Vereb; Michael Flynn

(57) ABSTRACT

Example methods and apparatus to determine phase-change pressures are disclosed. A disclosed example method includes capturing a fluid in a chamber, pressurizing the fluid at a plurality of pressures, measuring a plurality of transmittances of a signal through the fluid at respective ones of the plurality of pressures, computing a first magnitude of a first subset of the plurality of transmittances, computing a second magnitude of a second subset of the plurality of transmittances, comparing the first and second magnitudes to determine a phase-change pressure for the fluid.

19 Claims, 20 Drawing Sheets

U.S. PATENT DOCUMENTS

| | | | |
|---|---|---|---|
| 7,458,252 B2* | 12/2008 | Freemark et al. | 73/64.45 |
| 7,461,547 B2 | 12/2008 | Terabayashi et al. | |
| 8,051,706 B2* | 11/2011 | DiFoggio | 73/152.51 |
| 2002/0129936 A1* | 9/2002 | Cernosek | 166/264 |
| 2003/0015321 A1* | 1/2003 | Lim et al. | 166/263 |
| 2003/0080604 A1* | 5/2003 | Vinegar et al. | 299/14 |
| 2004/0026076 A1* | 2/2004 | Goodwin et al. | 166/66.6 |
| 2007/0187092 A1* | 8/2007 | Mullins et al. | 166/252.1 |
| 2008/0156088 A1 | 7/2008 | Hsu et al. | |
| 2008/0156486 A1 | 7/2008 | Ciglenec et al. | |
| 2009/0078036 A1* | 3/2009 | Terabayashi et al. | 73/152.55 |
| 2009/0078412 A1 | 3/2009 | Kanayama et al. | |
| 2009/0091320 A1* | 4/2009 | Flaum et al. | 324/303 |

OTHER PUBLICATIONS

Fujisawa et al, "Live Oil Sample Acquisition and Downhole Fluid Analysis," Chapter 22, Asphaltenes, Heavy Oils and Petroleomics, edited by O. Mullins, E. Sheu, A. Hammami and A. Marshall, Springer, 2007.

Stankiewicz et al., "Prediction of Asphaltene Deposition Risk in E&P Operations," 3rd International Symposium on Mechanisms and Mitigation of Fouling in Petroleum and Natural Gas Production, Mar. 10-14, 2002.

McCain, "The Properties of Petroleum Fluids," PennWell Publishing Company, 1990.

Mullins, "Asphaltenes in Crude Oil: Absorbers and/or Scatters in the Near-infared," Analytical Chemistry, vol. 62, 1990, p. 508-514. (7 pages).

Ruiz-Morales et al., "Electronic Absorption Edge of Crude Oils and Asphaltenes Analyzed by Molecular Orbital Calculations with Optical Spectroscopy," Energy and Fuels, vol. 21, 2007, p. 944-952. (9 pages).

Michaels et al., "Advances in Wireline Formation Testing," SPWLA 36th Annual Logging Symposium, Jun. 26-29, 1995. (11 pages).

Proett et al., "New Wireline Formation Testing Tool With Advanced Sampling Technology," SPE Reservoir Evaluation and Engineering, Apr. 2001. (12 pages).

Mullins, Oliver C. et al., Downhole Determination of GOR on Single-Phase Fluids by Optical Spectroscopy, SPWLA 42nd Annual Logging Symposium, Jun. 17-20, 2001.

Mullins, Oliver C. et al., Hydrocarbon Compositional Analysis In-Situ in Openhole Wireline Logging, SPWLA 45th Annual Logging Symposium, Jun. 6-9, 2004.

Betancourt, Soraya et al., Exploration Applications of Downhole Measurement of Crude Oil Composition and Fluorescence, SPE 87011, Kuala Lumpur, Malaysia, Mar. 29-30, 2004.

Fujisawa, Go et al., Analyzing Reservoir Fluid Composition In-Situ in Real-Time: Case Study in a Carbonate Reservoir, SPE 84092, Denver, Colorado, Oct. 5-8, 2003.

Elshahawi, H. et al., Insitu Characterization of Formation Fluid Samples—Case Studies, SPE 90932, Houston, Texas, Sep. 26-29, 2004.

Fujisawa, Go et al., Hydrocarbon Compositional Gradient Revealed by In-Situ Optical Spectroscopy, SPE 89704, Houston, Texas, Oct. 2, 2007.

Dong, C. et al., New Downhole Fluid Analyzer Tool for Improved Reservoir Characterization, SPE 108566, Aberdeen, Scotland, Sep. 4-7, 2007.

\* cited by examiner

| Test fluid | GOR (scf/stb) | API | Viscosity (cp) | Density (g/cm$^3$) |
|---|---|---|---|---|
| Live oil 1 | 3100 | 43.4 | 0.10-0.15 | 0.50-0.56 |
| Live oil 2 | 1090 | 32.3 | 0.55-0.80 | 0.67-0.72 |
| Live oil 3 | 640 | 27.5 | 0.90-1.30 | 0.73-0.78 |
| Live oil 4 | 210 | 24.7 | 5-8 | 0.81-0.84 |
| Gas condensate | 9630 | 52.6 | 0.05-0.07 | 0.38-0.44 |
| Asphaltene oil | 710 | 21.1 | | |

FIG. 5C

METHODS AND APPARATUS TO DETERMINE PHASE-CHANGE PRESSURES

BACKGROUND

Wellbores may be drilled to, for example, locate and produce hydrocarbons. During a drilling operation, it may be desirable to evaluate and/or measure properties of encountered formations, formation fluids and/or formation gasses. An example property is the phase-change pressure of a formation fluid, which may be a bubble point pressure, a dew point pressure and/or an asphaltene onset pressure depending on the type of fluid. In some cases, a drillstring is removed and a wireline tool deployed into the wellbore to test, evaluate and/or sample the formation(s), formation gas(ses) and/or formation fluid(s). In other cases, the drillstring may be provided with devices to test and/or sample the surrounding formation(s), formation gas(ses) and/or formation fluid(s) without having to remove the drillstring from the wellbore.

BRIEF DESCRIPTION OF THE DRAWINGS

FIGS. 5A-5C depict example properties of example fluids discussed in the present disclosure.

DETAILED DESCRIPTION

Figure 1:
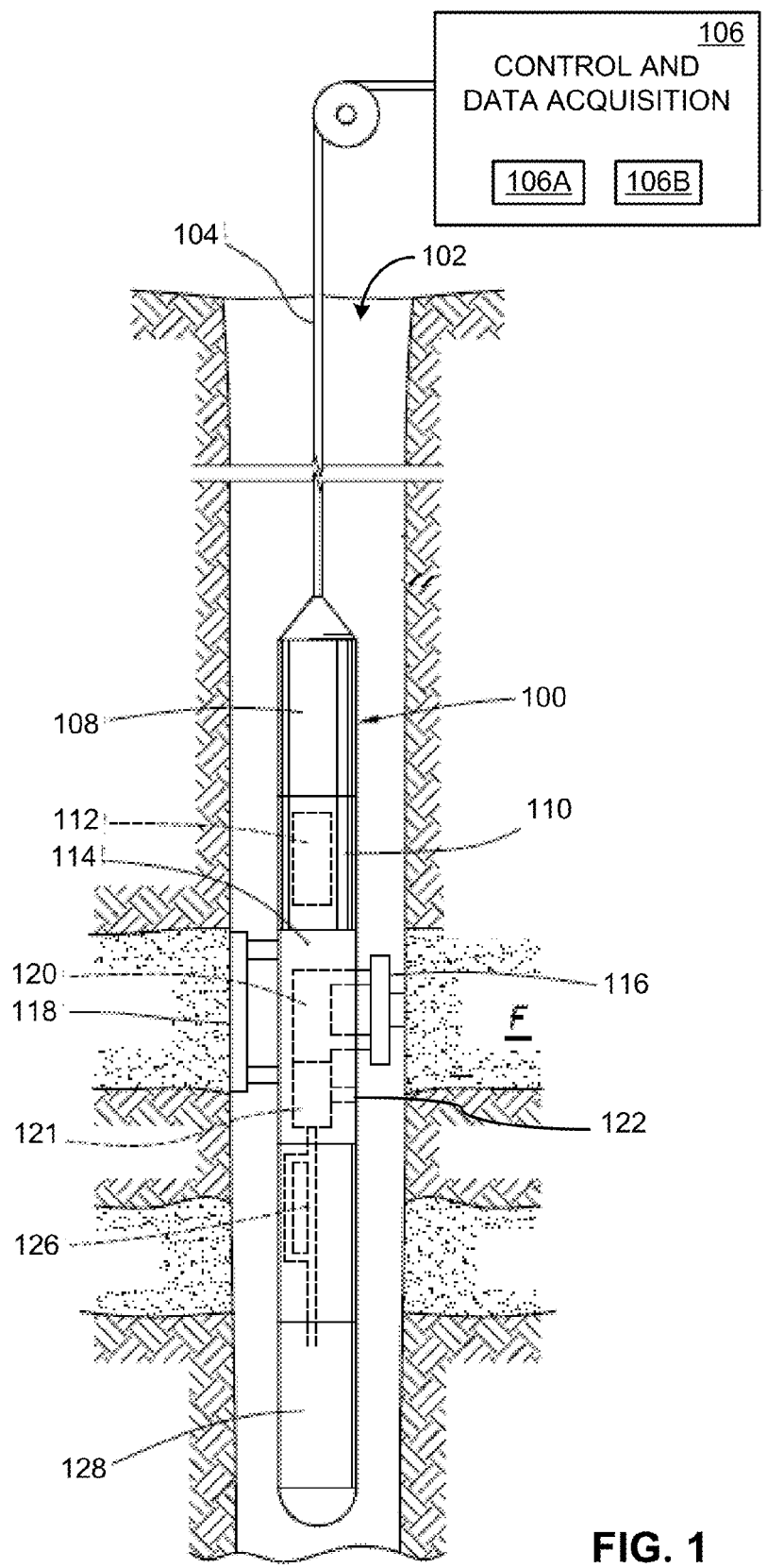
FIG. 1 depicts an example wellsite fluid analysis system according to one or more aspects of the present disclosure.

Certain examples are shown in the above-identified figures and described in detail below. The figures are not necessarily to scale and certain features and certain views of the figures may be shown exaggerated in scale or in schematic for clarity and/or conciseness. It is to be understood that while the following disclosure provides many different embodiments or examples for implementing different features of various embodiments, other embodiments may be implemented and/or structural changes may be made without departing from the scope of this disclosure. Further, while specific examples of components and arrangements are described below these are, of course, merely examples and are not intended to be limiting. In addition, the present disclosure may repeat reference numerals and/or letters in the various examples. This repetition is for the purpose of clarity and does not in itself dictate a relationship between the various embodiments and/or example configurations discussed. Moreover, the formation of a first feature over or on a second feature in the description that follows may include embodiments in which the first and second elements are implemented in direct contact, and may also include embodiments in which other elements may be interposed between the first and second elements, such that the first and second elements need not be in direct contact.

Methods and apparatus for analyzing formation fluid(s) are disclosed herein. The methods and apparatus of the present disclosure may be used to determine phase-change pressures of fluid(s) extracted from a subterranean formation into which a well has been drilled. In some cases, the formation fluid(s) may be brought to the surface and analyzed in a laboratory. In other cases, the formation fluid(s) may be analyzed in situ using a drillstring and/or wireline fluid analysis tool lowered into the well. Example phase-change and/or phase-transition pressures include a bubble point ($P_b$) pressure, a dew point ($P_d$) pressure and/or an asphaltene onset pressure (AOP), depending on the type(s) of fluid(s) being analyzed. As used herein, the detection and/or identification of the onset of phase-change of a fluid refers to the identification of the time and/or the pressure during a systematic depressurization or reductions in the pressure of the fluid at which a phase-change of the fluid occurs. While certain examples are described using systematic depressurization of the fluid, the example methods and apparatus disclosed herein may, additionally or alternatively, be implemented using systematic pressurization or increases in the pressure of the fluid. Accordingly, throughout this disclosure references are made to systematic (de-)pressurization meaning that either a systematic pressurization or a systematic depressurization may be implemented.

In the present disclosure, fluid analysis tools may induce a prescribed rate of change of the pressure of a formation fluid trapped, captured and/or held in the fluid analysis tool. The fluid may be, for example, depressurized according to a predetermined pressure versus time profile. The fluid analysis tool may include a pressure changing device configured to controllably induce the prescribed pressure change. The phase-change pressure of the fluid may be determined using light scattering measured at a plurality of times during the depressurization of the fluid. During a first portion or phase of the depressurization of the fluid, the amount of light transmitted through the fluid may be uninterrupted (e.g., substantially unscattered), provided that the fluid remains in its single phase. That is, assuming the pressure of the fluid during this first portion or phase remains above the phase-change pressure. In contrast, when the pressure of the fluid reaches the phase-change pressure, gas bubbles, liquid droplets and/or asphaltene particles may emerge from the fluid and may begin scattering light. When the light passing through the fluid is scattered by the gas bubbles, liquid droplets and/or asphaltene particles, light transmittance through the fluid may be reduced. Detection of the reduction in light transmittance may be used to detect the onset of the phase-change. While the examples described herein utilize a scattering detector comprising a photo-detector to measure light transmittance (or conversely light scattering) through a fluid, the example methods and apparatus disclosed herein may be implemented using any number and/or type(s) of additional and/or alternative sensor(s) and/or detector(s) configured to measure scattering and/or transmittability of any number and/or type(s) of signals through a fluid. For example, an acoustic sensor may be implemented to detect gas bubbles, liquid droplets and/or asphaltene particles based on the scattering of an acoustic signal by any gas bubbles, liquid droplets and/or asphaltene particles present in the fluid. Another example sensor is an electrical resistivity sensor configured to measure a change in resistivity of the fluid in the presence or absence of gas bubbles, liquid droplets and/or asphaltene particles.

The methods and apparatus of the present disclosure may not require measuring a volume of the formation fluid to determine the phase-change pressure of the formation fluid. The foregoing may be advantageous when, for example, a determination of the formation fluid volume is difficult to obtain and/or is unknown. The determination of the formation fluid volume may be difficult to ascertain when the formation fluid is not sealed in a test volume, flowline and/or chamber, and/or if an enclosure containing the formation fluid is relatively compliant under pressure compared to the compressibility of the formation fluid. However, the volume of the formation fluid may optionally be estimated, measured and/or utilized within the scope of the present disclosure. Further, the examples described herein do not rely on, require and/or depend on a detectable transition in a pressure-versus-volume curve. As shown below, pressure-versus-volume data may be smooth at the phase-change pressure, making phase-change detection from pressure-versus-volume data unreliable and/or difficult.

FIG. 1 depicts an example wellsite system according to one or more aspects of the present disclosure. The example wellsite of FIG. 1 may be situated onshore (as shown) or offshore. The example wellsite system may include a wireline assembly 100, which may be configured to determine phase-change pressures of formation fluid(s) extracted from a subterranean formation F into which a wellbore 102 has been drilled.

The example wireline assembly 100 of FIG. 1 may be suspended in the wellbore 102 from the lower end of a multi-conductor cable 104, which may be spooled on a winch (not shown) at the Earth's surface. At the surface, the cable 104 may be communicatively and/or electrically coupled to a control and data acquisition system 106. The example control and data acquisition system 106 of FIG. 1 may include a controller 106A having an interface configured to receive commands from a surface operator. The control and data acquisition system 106 may further include a processor 106B configured to determine phase-change pressures of formation fluid(s) extracted from the subterranean formation F.

The example wireline assembly 100 of FIG. 1 may have an elongated body 108 and may include a telemetry module 110 and/or a formation tester 114. Although the example telemetry module 110 of FIG. 1 is shown as being implemented separate from the example formation tester 114, the telemetry module 110 may alternatively be implemented by the formation tester 114. Further, additional and/or alternative components, modules and/or tools may also be implemented by the wireline assembly 100.

The example formation tester 114 of FIG. 1 may include a selectively extendable fluid admitting assembly and/or probe 116 and/or a selectively extendable tool anchoring member 118 that may be arranged on opposite sides of the example body 108. As shown, the fluid admitting assembly 116 may be configured to selectively seal off and/or isolate selected portions of the wall of the wellbore 102 and to fluidly couple components of the formation tester 114 such as, for example, a pump 121, to the formation F. Thus, the formation tester 114 may be used to obtain fluid(s) from the formation F.

The example formation tester 114 of FIG. 1 may also include a fluid sensing unit 120 through which formation fluid(s) may flow. The example fluid sensing unit 120, through which the obtained fluid(s) may flow, may be configured to measure properties of the fluid(s) extracted from the formation F. It should be appreciated that the fluid sensing unit 120 may include any combination of past, present and/or future-developed sensors within the scope of the present disclosure. The fluid(s) may thereafter be expelled through a port 122 into the wellbore 102 and/or the fluid(s) may be sent to one or more fluid collecting chambers disposed in a sample carrier module 128. The fluid collecting chambers may receive and retain samples of the formation fluid(s) for subsequent retrieval and/or testing at the surface and/or at a testing facility and/or laboratory.

In the illustrated example of FIG. 1, the example formation tester 114 implements a fluid isolation and analysis tool 126 that is fluidly coupled to the fluid admitting assembly 116 and the pump 121. The example fluid isolation and analysis tool 126 of FIG. 1 may include a pressure changing device 404 (FIG. 4A) configured to controllably induce and/or affect a pressure change of a formation fluid(s) extracted from the subterranean formation F. The example fluid isolation and analysis tool 126 may also include a scattering detector 444 (FIG. 4A) configured to measure the amount of light that passes through the fluid(s). The fluid isolation and analysis tool 126 may further include one or more additional sensors that may be used to assist in the determination of phase-change pressures. Example additional sensors that may be implemented include, but are not limited to, a multi-channel spectrometer, a density/viscosity (DV) sensor, such as a DV rod, configured to measure fluid density and/or fluid viscosity, a pressure gauge, and/or a temperature gauge.

The example telemetry module 110 of FIG. 1 may comprise a downhole control system 112 communicatively coupled to the example control and data acquisition system 106. In the illustrated example of FIG. 1, the control and data acquisition system 106 and/or the downhole control system 112 may be configured to control the fluid admitting assembly 116 and/or the extraction of fluid(s) from the formation F by, for example, selecting a pumping rate of the pump 121. The control and data acquisition system 106 and/or the downhole control system 112 may further be configured to direct the example fluid isolation and analysis tool 126 to induce or affect a targeted rate of change of the pressure of the formation fluid in the fluid isolation and analysis tool 126, and/or to measure light transmittance of the fluid during the systematic pressure change(s).

The example control and data acquisition system 106 and/or the example downhole control system 112 of FIG. 1 may be further configured to analyze and/or process data obtained, for example, from the fluid sensing unit 120 and/or from other downhole sensors disposed in the example fluid isolation and analysis tool 126. Such data may be stored and/or communicated to the surface for subsequent retrieval and/or analysis. In particular, a phase-change pressure of the formation fluid in the fluid isolation and analysis tool 126 may be determined using data collected by the scattering detector 444 during (de-)pressurization of the formation fluid.

As depicted in FIG. 1, the example wireline assembly 100 may include multiple downhole modules that are operatively connected together. Downhole tools often include several modules (i.e., sections of the wireline assembly 100 that perform different functions). Additionally, more than one downhole tool or component may be combined on the same wireline to accomplish multiple downhole tasks during the same wireline run. The modules are typically connected by field joints. For example, one module of a formation testing tool typically has one type of connector at its top end and a second type of connector at its bottom end. The top and bottom connectors are made to operatively mate with each other. By using modules and/or tools with similar arrangements of connectors, all of the modules and tools may be connected end-to-end to form the wireline assembly 100. A field joint may provide an electrical connection, a hydraulic connection, and/or a flowline connection, depending on the requirements of the tools on the wireline. An electrical connection typically provides both power and communication capabilities.

In practice, the wireline tool assembly 100 may include several different components, some of which may include two or more modules (e.g., a sample module and a pumpout module of a formation testing tool). In this disclosure, the term "module" is used to describe any of the separate and/or individual tool modules that may be connected in the wireline assembly 100. The term "module" refers to any part of the wireline assembly 100, whether the module is part of a larger tool or a separate tool by itself. It is also noted that the term "wireline tool" is sometimes used in the art to describe the entire wireline assembly 100, including all of the individual tools that make up the assembly. In this disclosure, the term "wireline assembly" is used to prevent any confusion with the individual tools that make up the wireline assembly (e.g., a coring tool, a formation testing tool, and a nuclear magnetic resonance (NMR) tool may all be included in a single wireline assembly).

Figure 2:
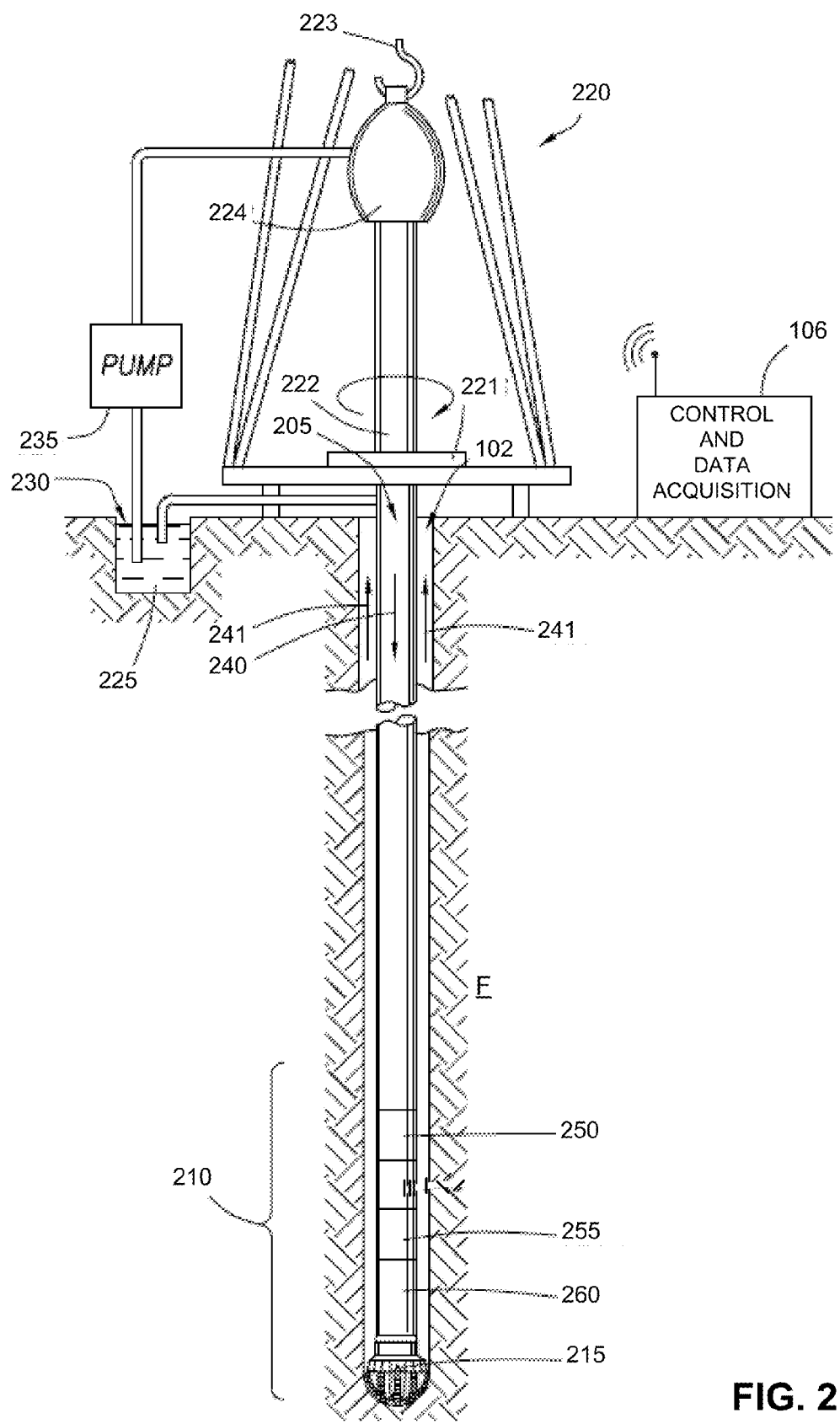
FIG. 2 depicts another example wellsite fluid analysis system according to one or more aspects of the present disclosure.

FIG. 2 depicts another example wellsite fluid analysis system according to one or more aspects of the present disclosure, which may be employed onshore (as shown) and/or offshore. In the example wellsite system of FIG. 2, the example borehole 102 is formed in the subsurface formation F by rotary and/or directional drilling. In the illustrated example of FIG. 2, a drillstring 205 is suspended within the example borehole 102 and has a bottom hole assembly (BHA) 210 having a drill bit 215 at its lower end. A surface system includes a platform and derrick assembly 220 positioned over the borehole 102. The assembly 220 may include a rotary table 221, a kelly 222, a hook 223 and/or a rotary swivel 224. The drillstring 205 may be rotated by the rotary table 221, energized by means not shown, which engages the kelly 222 at the upper end of the drillstring 205. The example drillstring 205 may be suspended from the hook 223, which may be attached to a traveling block (not shown) and through the kelly 222 and the rotary swivel 224, which permits rotation of the drillstring 205 relative to the hook 223. Additionally or alternatively, a top drive system may be used.

In the example of FIG. 2, the surface system may also include drilling fluid 225, which is commonly referred to in the industry as mud, stored in a pit 230 formed at the wellsite. A pump 235 may deliver the drilling fluid 225 to the interior of the drillstring 205 via a port (not shown) in the swivel 224, causing the drilling fluid 225 to flow downwardly through the drillstring 205 as indicated by the directional arrow 240. The drilling fluid 225 may exit the drillstring 205 via water courses, nozzles, jets and/or ports in the drill bit 215, and then circulate upwardly through the annulus region between the outside of the drillstring 205 and the wall of the borehole 102, as indicated by the directional arrows 241. The drilling fluid 225 may be used to lubricate the drill bit 215 and/or carry formation cuttings up to the surface, where the drilling fluid 225 may be cleaned and returned to the pit 230 for recirculation. The drilling fluid 225 may also be used to create a mudcake layer (not shown) on the walls of the borehole 102. It should be noted that in some implementations, the drill bit 215 may be omitted and the bottom hole assembly 210 may be conveyed via tubing and/or pipe.

The example BHA 210 of FIG. 2 may include, among other things, any number and/or type(s) of downhole tools, such as any number and/or type(s) of logging-while-drilling (LWD) modules (one of which is designated at reference numeral 250), and/or any number and/or type(s) of measuring-while-drilling (MWD) modules (one of which is designated at reference numeral 255), a rotary-steerable system or mud motor 260, and/or the example drill bit 215. MWD typically refers to measuring the drill bit trajectory as well as wellbore temperature and pressure, while LWD refers to measuring formation and/or formation fluid parameters or properties, such as a resistivity, a porosity, a permeability, a viscosity, a density, a phase-change pressure, and a sonic velocity, among others. Real-time data, such as the formation pressure, allows the drilling company to make decisions about drilling mud weight and composition, as well as decisions about drilling rate and weight-on-bit during the drilling process. While LWD and MWD have different meanings to those of ordinary skill in the art, that distinction is not germane to this disclosure, and therefore this disclosure does not distinguish between the two terms. Furthermore, LWD and MWD need not be performed while the drill bit is actually cutting through the formation F. For example, LWD and MWD may occur during interruptions in the drilling process, such as when the drill bit 215 is briefly stopped to take measurements, after which drilling resumes. Measurements taken during intermittent breaks in drilling are still considered to be made "while-drilling" because they do not require the drill string to be tripped, that is, removed from the wellbore 102.

The example LWD module 250 of FIG. 2 is housed in a special type of drill collar, as it is known in the art, and may contain any number and/or type(s) of logging tool(s), measurement tool(s), sensor(s), device(s), formation evaluation tool(s), fluid analysis tool(s), and/or fluid sampling device(s). For example, the LWD module 250 may be configured to measure light transmittance of a formation fluid while the fluid is systematically pressurized and/or depressurized to determine a phase-change pressure of the formation fluid. The LWD module 250 may include capabilities for measuring, processing, and/or storing information, as well as for communicating with the MWD module 260 and/or directly with surface equipment, such as the example logging and control computer 106. While a single LWD module 250 is depicted in FIG. 2, it will also be understood that more than one LWD module may be implemented. The example LWD module 250 of FIG. 2 may include a processor 470 (FIG. 4A) configured to implement one or more aspects of the present disclosure.

The example MWD module 255 of FIG. 2 is also housed in a special type of drill collar and contains one or more devices for measuring characteristics of the drillstring 205 and/or the drill bit 215. The example MWD tool 255 may also include an apparatus (not shown) for generating electrical power for use by the downhole system 210. Example devices to generate electrical power include, but are not limited to, a mud turbine generator powered by the flow of the drilling fluid, and a battery system. Example measuring devices include, but are not limited to, a weight-on-bit measuring device, a torque measuring device, a vibration measuring device, a shock measuring device, a stick/slip measuring device, a direction measuring device, and an inclination measuring device. Additionally or alternatively, the MWD module 255 may include an annular pressure sensor, and/or a natural gamma ray sensor. The MWD module 255 may include capabilities for measuring, processing, and storing information, as well as for communicating with the logging and control unit 106. For example, the MWD module 255 and the logging and control unit 106 may communicate information either way (i.e., uplink and downlink) using any past, present or future two-way telemetry system such as a mud-pulse telemetry system, a wired drillpipe telemetry system, an electromagnetic telemetry system and/or an acoustic telemetry system. While not shown in FIG. 2, the example control and data acquisition system 106 of FIG. 2 may include the example controller 106A and/or the example processor 106B discussed above in connection with FIG. 1.

Figure 3:
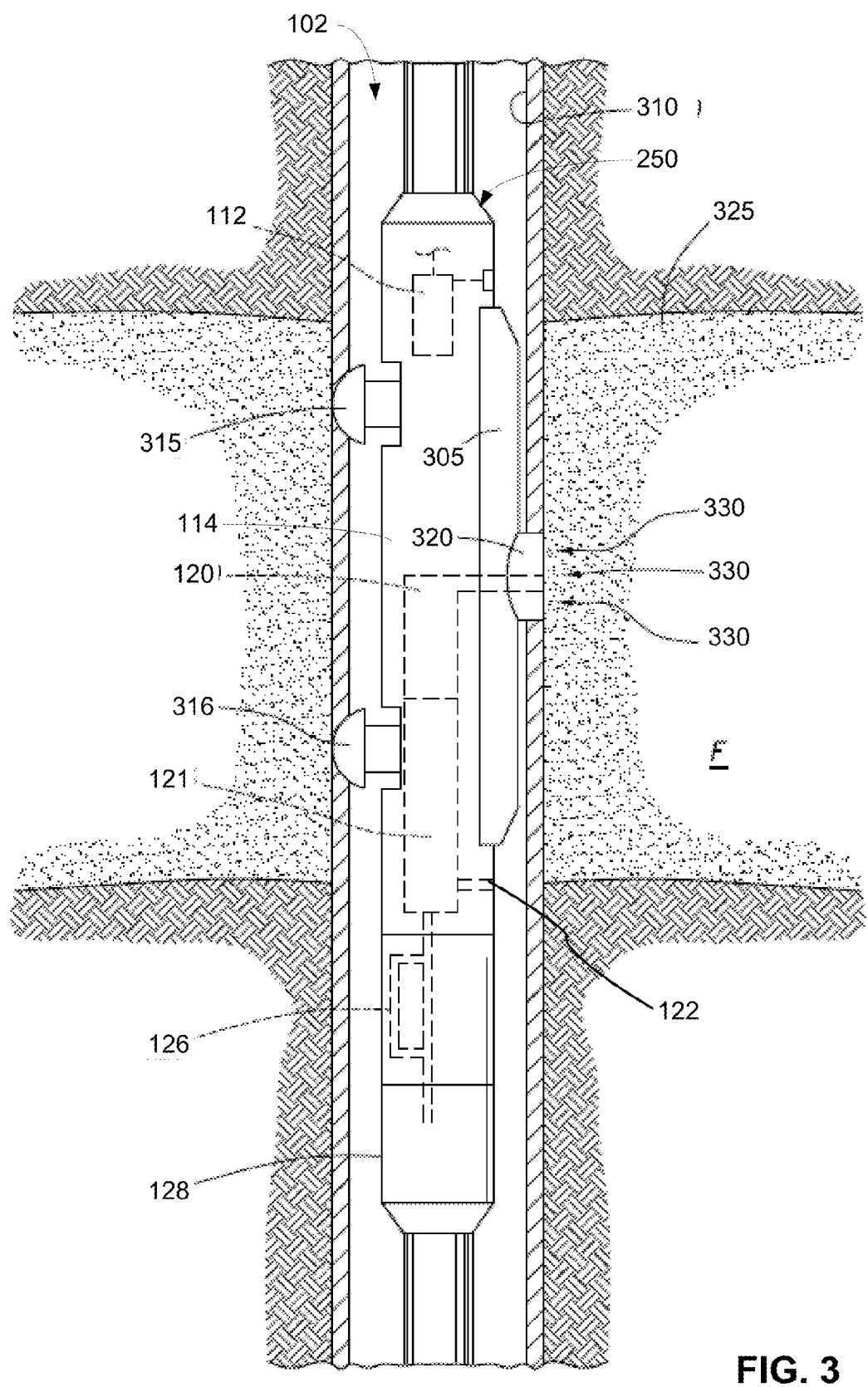
FIG. 3 depicts an example drillstring fluid analysis tool according to one or more aspects of the present disclosure.

FIG. 3 depicts an example manner of implementing the example LWD module 250 of FIG. 2. Because some elements of the example LWD module 250 of FIG. 3 are identical to those discussed above in connection with FIG. 1, the description of identical elements is not repeated here. Instead, identical elements are designated with identical reference numerals in FIGS. 1 and 3, and the interested reader is referred back to the descriptions presented above in connection with FIG. 1 for a complete description of those like-numbered elements.

The example LWD module 250 of FIG. 3 may include a stabilizer having one or more blades 305 configured to engage a wall 310 of the wellbore 102. The example LWD module 250 may also include one or more backup pistons, two of which are designated at reference numerals 315 and 316, to assist in applying a force to push and/or move the LWD module 250 against the wall 310 of the wellbore 102. Example blades 305 and backup pistons 315 and 316 are described in U.S. Pat. No. 7,114,562, which is hereby incorporated herein by reference in its entirety. However, any number and/or type(s) of additional and/or alternative blades and/or pistons may be used to implement the LWD module 250.

The example LWD module 250 of FIG. 3 may include a fluid admitting assembly 320, which may extend from the stabilizer blade 305. The fluid admitting assembly 320 may be configured to selectively seal off or isolate selected portions of the wall 310 of the wellbore 102 to fluidly couple the LWD module 250 to an adjacent formation F. Once the fluid admitting assembly 310 fluidly couples to the adjacent formation F, various measurements may be conducted on the adjacent formation F and/or a fluid 330 drawn from the formation F. For example, a pressure parameter may be measured by performing a pretest.

While the wireline assembly 100 of FIG. 1 and the LWD module 250 of FIG. 3 are depicted having one fluid admitting assembly 116, 320, respectively, a plurality of fluid admitting assemblies may alternatively be provided on the wireline assembly 100 and/or the LWD module 250. In particular, the fluid admitting assembly 116 of FIG. 1 and/or the fluid admitting assembly 320 of FIG. 3 may be implemented with a guarded and/or focused fluid admitting assembly, for example, as shown in U.S. Pat. No. 6,964,301, which is hereby incorporated by reference in its entirety. In such cases, the fluid isolation and analysis tool 126 may, for example, be fluidly coupled to a central inlet and/or port of the guarded or focused fluid admitting assembly 116, 320.

Figure 4A:
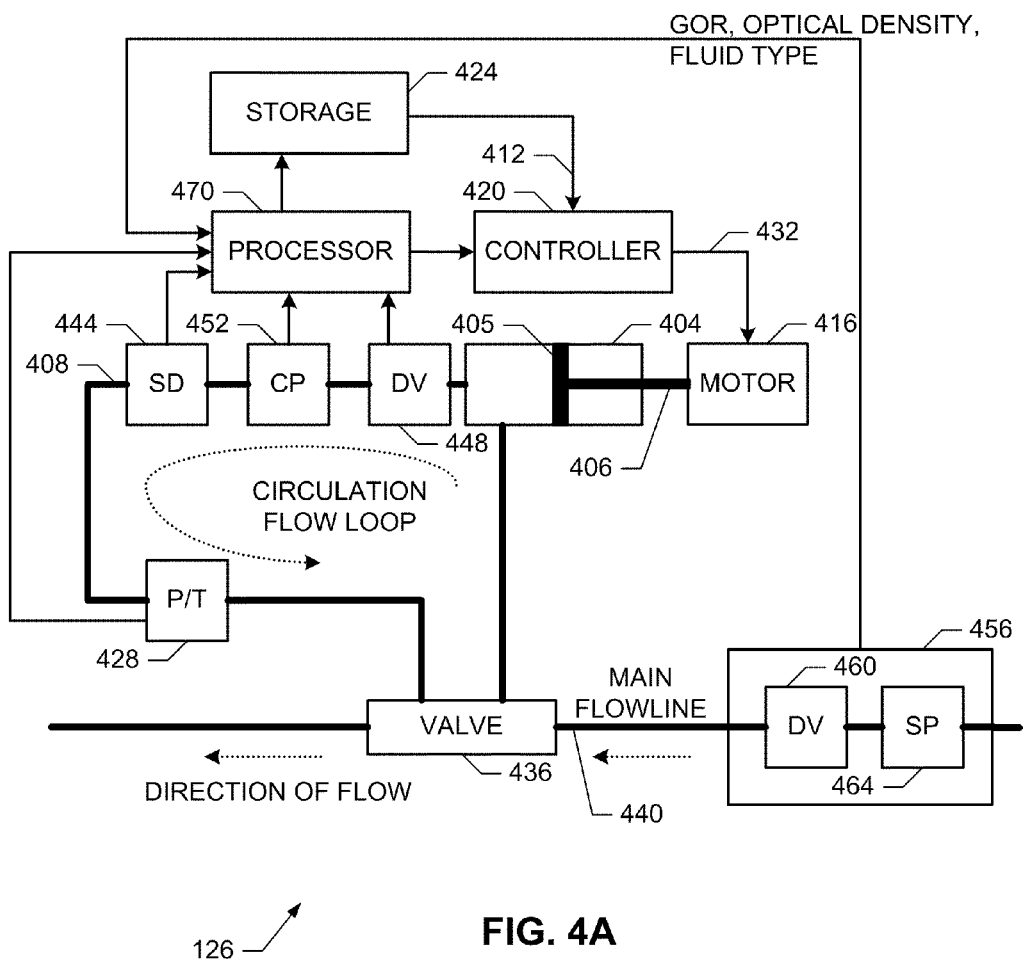
FIGS. 4A-4C depicts an example fluid isolation and analysis tool according to one or more aspects of the present disclosure.
Figure 4B:
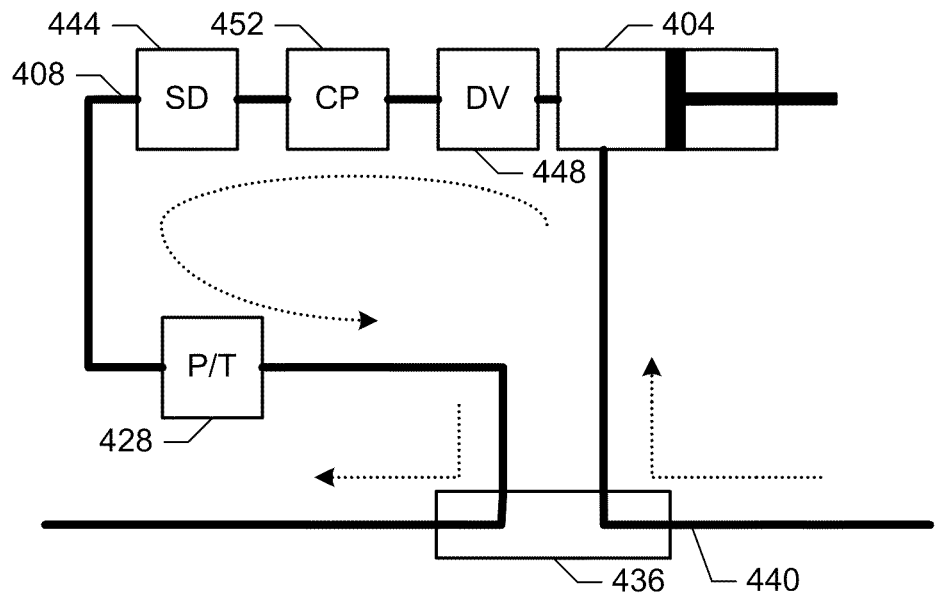
Figure 4C:
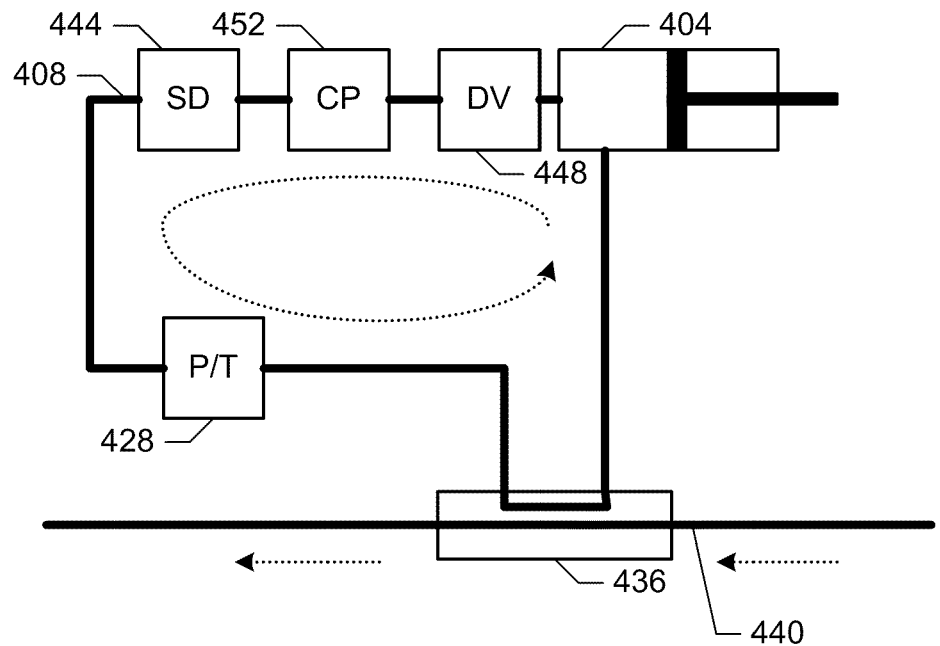

FIGS. 4A-C depict an example manner of implementing the example fluid isolation and analysis tool 126 of FIGS. 1 and 3. While the example fluid isolation and analysis tool 126 of FIGS. 4A-C is described with reference to the example downhole tools 100 and 250 of FIGS. 1-3, the example methods and apparatus disclosed herein to determine phase-change pressures may, additionally or alternatively, be implemented in a laboratory located at a wellsite and/or elsewhere.

The fluid isolation and analysis tool 126 of FIG. 4A may include the pressure changing device 404, which may be configured to controllably induce and/or affect a systematic pressure change in a test chamber, volume, and/or flowline 408 based on at least one prescribed rate 412. In other words, the example pressure changing device 404 of FIGS. 4A-4C may be configured to induce or affect a targeted rate of change of the pressure of a fluid trapped and/or captured in the test flowline 408 according to the pressure rate profile 412. The example pressure changing device 404 may include a sliding piston 405 configured to alter the pressure in the test flowline 408. The example piston 405 may be affixed to a ram 406, which is configured to reciprocate upon rotation of, for example, an electric motor 416 such as a stepper motor. For example, an output shaft (not shown) of the example motor 416 may be operatively coupled to a gear box (not shown) that engages the ram 406 to move the example piston 405. As used herein, the fluid trapped and/or captured in the test flowline 408 includes fluid trapped and/or captured in the pressure changing device 404.

The example fluid isolation and analysis tool 126 of FIGS. 4A-4C may further include a controller 420 to induce pressure changes in the test flowline 408 based on fluid pressures measured in the test flowline 408. For example, the example controller 420 of FIG. 4A may be provided with values 412 representing prescribed and/or targeted rates of pressure change. The pressure changes may be carried out in a stepwise and/or continuous fashion. The prescribed pressure change rates 412 may be retrieved from a computer readable medium or any storage medium 424, and/or may be entered by an operator via an interface provided by the control and data acquisition system 106 of FIGS. 1 and 2. The example fluid isolation and analysis tool 126 may include any type of pressure and temperature (P/T) sensor 428 configured to measure the pressure and/or the temperature of the fluid in the test flowline 408 at a plurality of times $\{t_0, t_1, t_2, \ldots, t_n\}$, and to communicate the measured pressures to the controller 420. The example processor 470 may be configured to determine, measure and/or compute actual rates of the pressure change in the test flowline 408 from the measured pressures. For example, the actual rates of the pressure change may be determined by fitting a curve to a portion of the measured pressures at the plurality of times $\{t_0, t_1, t_2, \ldots, t_n\}$, and determining a slope of the curve. The fitting may be performed using, for example, a least-squares algorithm such as the Savitzky-Golay filter or an iterative re-weighted least-squares algorithm.

The example controller 420 of FIG. 4A may be configured to drive the example motor 416 via control signals 432 representing prescribed angular speeds and/or rotations per minute (rpm). The controller 420 may be configured to execute instructions stored on the computer readable medium 424 that, when executed, cause the fluid isolation and analysis tool 126 to induce or affect the targeted rates 412 of pressure change of the formation fluid in the test flowline 408. For example, the angular speed of the motor 416 may be selected such that the rate of pressure change of the formation fluid in the test flowline 408 resulting from the motor rotation reduces the differences between the target pressure change ranges and the actual pressure change rates computed by the processor 470. The controller 420 may be configured to implement a feedback control process to determine the control signals 432. An example feedback control process is a proportional-integral-derivative (PID) controller, which is commonly used in industrial control applications.

The fluid isolation and analysis tool 126 of FIGS. 4A and 4B may further include a four-port, two-position valve 436. The example four-port two-position valve 436 of FIGS. 4A-4C may be used to selectively flow a formation fluid admitted into the fluid isolation and analysis tool 126 via a main flowline 440 through the test flowline 408 (as shown in FIG. 4B), and/or to seal, trap and/or capture a portion of the formation fluid in the test flowline 408 (as shown in FIG. 4C).

The example test flowline 408 of FIGS. 4A-4C may include any number and/or type(s) of sensor(s), tools(s) and/or fluid analysis module(s), in addition to or instead of the P/T sensor 428, to measure other properties of the formation fluid in the test flowline 408. Other example sensor(s) that may be implemented include, but are not limited to, the scattering detector (SD) 444, which may be configured to measure the amount of light that passes through the formation fluid, and/or a DV sensor 448, which may be configured to measure fluid density and/or viscosity. The example sensors 428, 444 and 448, a circulating pump (CP) 452, the example pressure changing device 404, and the example valve 436 may be arranged along the test flowline 408 in any order.

The example test flowline 408 of FIGS. 4A-4C may be provided with the CP 452. The example CP 452 of FIGS. 4A-4C may be used to agitate the formation fluid in the test flowline 408 by inducing a flow of formation fluid in the test flowline 408. For example, a portion of the formation fluid sealed in the test flowline 408 may be circulated in the test flowline 408, as shown in FIG. 4C. The example CP 452 may help to mix and/or agitate the fluid in the test flowline 408 so that any phase-changes (e.g., bubble formation) may be sensed by all the example sensors 428, 444 and 448 of the test flowline 408.

To measure any number and/or type(s) of additional fluid properties, the example main flowline 440 may include any number and/or type(s) of additional sensor(s), tools(s) and/or fluid analysis module(s). Additional sensor(s), tool(s) and/or fluid analysis module(s) that may be implemented include, but are not limited to the Schlumberger InSitu Fluid Analyzer™ 456, which may include, among other things, a DV sensor 460 and a multi-channel spectrometer (SP) 464. The example IFA 456 may be used to measure and/or determine, among other things, a gas/oil ratio (GOR), an optical density, and/or a fluid type. While in the illustrated example of FIG. 4A, the IFA 456 is implemented upstream from the fluid isolation and analysis tool 126 it may, alternatively, be implemented downstream from the fluid isolation and analysis tool 126.

The fluid isolation and analysis tool 126 of FIG. 4A may comprise a processor 470 communicatively coupled to any or all of the example sensors 428, 444, 448, 456, 460 and 464. In cases where the fluid isolation and analysis tool 126 is part of any of the example downhole tools 100 and/or 250 of FIGS. 1, 2, and 3, the example processor 470 may be implemented within the downhole tool 100 and/or 250. Additionally or alternatively, the processor 470 may be implemented at the Earth's surface by, for example, the example processor 106B of the example control and data acquisition system 106. The example processor 470 of FIG. 4 may be configured to determine, based on the measurements taken by one or more of the example sensors 428, 444, 448, 456, 460 and 464 during a systematic (de-)pressurization of the fluid in the test flowline 408, the phase-change pressure of the fluid in the test flowline 408. For example, the processor 470 may be configured to execute instructions stored on, for example, the storage or tangible computer readable medium 424 that, when executed, cause the processor 470 to carry out the example process of FIGS. 16A and 16B. Phase-change pressures and/or phase-change onset points may be stored in the example storage 424 for subsequent retrieval and/or processing at the surface, and/or may be transmitted via telemetry to the example control and data acquisition system 106.

While the example controller 420 of FIG. 4A systematically pressurizes and/or depressurizes the fluid in the test flowline 408 according to the pressure rates 412, one or more of the example sensors 428, 444, 448 may measure one or more properties of the fluid in the test flowline 408 at corresponding ones of the times $\{t_0, t_1, t_2, \ldots, t_n\}$. For example, the scattering sensor 444 may measure a plurality of light transmissions $\{x_0, x_1, x_2, \ldots x_n\}$ through the fluid in the test flowline 408 for respective ones of the times $\{t_0, t_1, t_2, \ldots, t_n\}$, which correspond to respective ones of the fluid pressures measured by the P/T sensor 428. The other example sensors 456, 460 and 464 may likewise measure other properties of the fluid. In general, the example fluid isolation and analysis tool 126 may measure, during a systematic (de-)pressurization process, pressure and temperature versus time using the example P/T sensor 428, viscosity and density versus time using the example DV sensor 448, scattering detector response versus time using the example SD 444, and/or (de-)pressurization rate and volume versus time.

The phase-change pressure of the fluid in the test flowline 408 may be determined from the measured light transmittances $\{x_0, x_1, \ldots x_n\}$. During depressurization of the fluid, the amount of light transmitted through the fluid may be substantially constant, provided that the fluid remains in its single phase during depressurization. However, when the pressure of the fluid reaches a phase-change pressure, gas bubbles, liquid droplets and/or asphaltene particles may emerge from the fluid and may begin scattering light. When the light passing through the fluid is scattered, the light transmittance of the fluid may be reduced. Detection of a change in the light transmittance of the fluid may be used by, for example, the processor 470 to detect the onset of the phase-change.

Figure 5A:
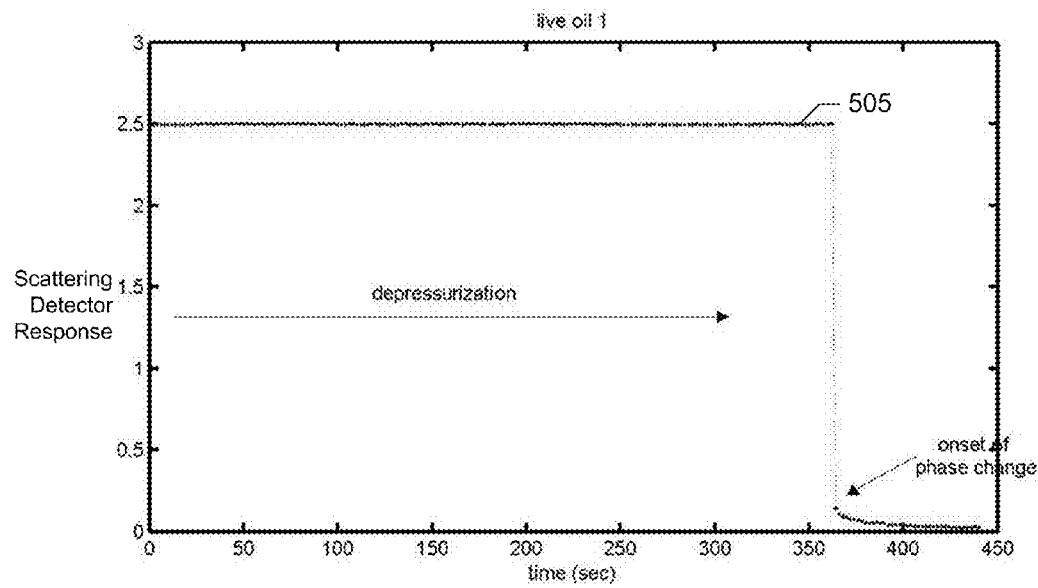
Figure 5B:
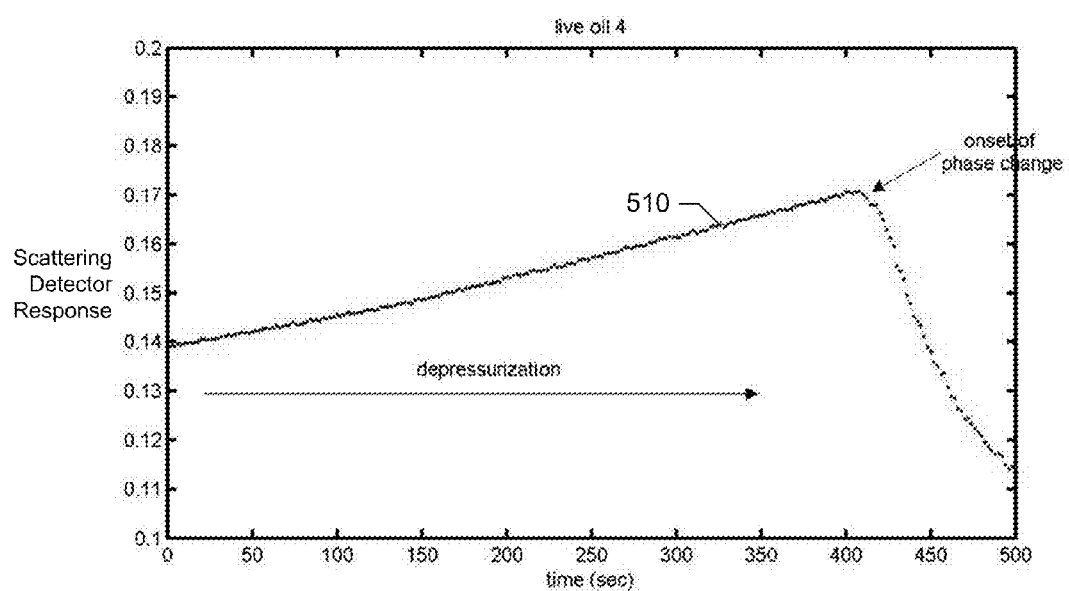

FIGS. 5A and 5B show scattering detector responses 505 and 510, measured by the example sensor 444 during depressurization of two different live fluids, respectively. Properties of these two example live fluids as well as other example fluids discussed herein are shown in FIG. 5C. As used herein, a scattering detector response represents a ratio of the voltage used to power a lamp to generate a transmitted light signal and a photo-detector output voltage of the SD 444 representing the amount of light that passed through the fluid. The ratio, rather than the photo-detector output voltage, may be used to reduce or minimize any effect(s) caused by a possibly changing power supply voltage of the lamp during (de-)pressurization. Therefore, the scattering detector response represents light transmittance through the fluid in the test flowline 408. While in the example graphs depicted throughout this disclosure, the direction of depressurization is synchronized with the progression of time, the fluid may alternatively be pressurized in synchronization with the progression of time. Before the onset of phase-change is reached, the response may be either flat (as shown in FIG. 5A) or sloped (as shown in FIG. 5B) as the pressure in the flow flowline 408 decreases. Differences in the responses 505 and 510 may be caused by a combined effect of color absorption, fluid compressibility and fluid density. An example scattering detector 444 uses a transmitted light wavelength of 1600 nanometers (nm), which is a wavelength at which the absorption of transmitted light may be affected by the electronic excitation, color effect of the fluid and/or light scattering. For gas condensate and light oil (such as shown in FIG. 5A), there is little electronic excitation absorption and/or color absorption at this wavelength, whereas for a darker and heavier live oil (as shown in FIG. 5B) the absorption caused by electronic excitation may be discernible. As the density of the fluid decreases with decreasing pressure during depressurization, the absorption of transmitted light decreases and as a result, the light transmittance 510 may increase for the darker and heavier live oil as shown in FIG. 5B. For gas condensate and light oil, however, there may be little change in light transmittance 505 by electronic excitation even though the density of fluid decreases during depressurization. Therefore, the scattering detector response 505 may remain nearly flat for pressures greater than the onset of phase-change, as shown in FIG. 5A.

When the onset of phase-change is reached, the light passing through the fluid may be partially or wholly scattered and, consequently, the scattering detector responses 505 and 510 decrease as shown in FIGS. 5A and 5B. In response to the emerging gas bubbles, the reduction in light transmittance may decrease abruptly as shown in FIG. 5A or may gradually decay as shown in FIG. 5B. The example methods and apparatus disclosed herein may be configured to automatically detect the onset of phase-change in either situation. The example methods and apparatus disclosed herein may use fluid properties measured by one or more of the other sensors 428, 448, 456, 460 and/or 464 to confirm, collaborate and/or quality check a phase-change pressure determined based on light transmittance measurements.

Denoting $x_i$ as the scattering detector response at the $i^{th}$ time index during (de-)pressurization, the example processor 470 of FIG. 4A may compute an energy ratio $e_i$, which may be expressed mathematically as:

$$e_i = 10 * \log_{10}\left(\frac{\sum_{k=i-w}^{k=i-1} x_k^2}{\sum_{k=i}^{k=i+w-1} x_k^2}\right) \quad \text{EQN (1)}$$

where the denominator within the parentheses is called the front energy (FE) and the numerator is called the back energy (BE), respectively, at the time index i, and w is a window size. The example energy ratio $e_i$ of EQN (1) has units of decibels (dB). The FE represents the energy of the light transmittances $x_i$ in a front energy window that includes the current time index i and extends forward w−1 samples. The BE represents the energy of the light transmittances $x_i$ in a back energy window that includes the preceding time index i−1 and extends backwards w−1 samples. Note that before the onset of phase-change is reached, the ratio in the parentheses of EQN (1) should be less than or equal to 1 and, therefore, the energy ratio $e_i$ is less than or equal to zero. However, when phase-change onset is reached, the energy ratio $e_i$ will increase and will become larger than zero. Accordingly, the processor 470 may compare the energy ratio $e_i$ to a threshold to detect the onset of phase-change.

In practice, the energy ratio $e_i$ of EQN (1) may be efficiently computed. For example, by defining a cumulative sum of energy $$ce_i = \sum_{k=1}^{k=i} x_k^2, \quad \text{EQN (2)}$$

the energy ratio $e_i$ can be expressed as $$e_i = 10 * \log_{10}\left(\frac{ce_{i-1} - ce_{i-w-1}}{ce_{i+w-1} - ce_{i-1}}\right). \quad \text{EQN (3)}$$

Figures 6A, 6B, 6C:
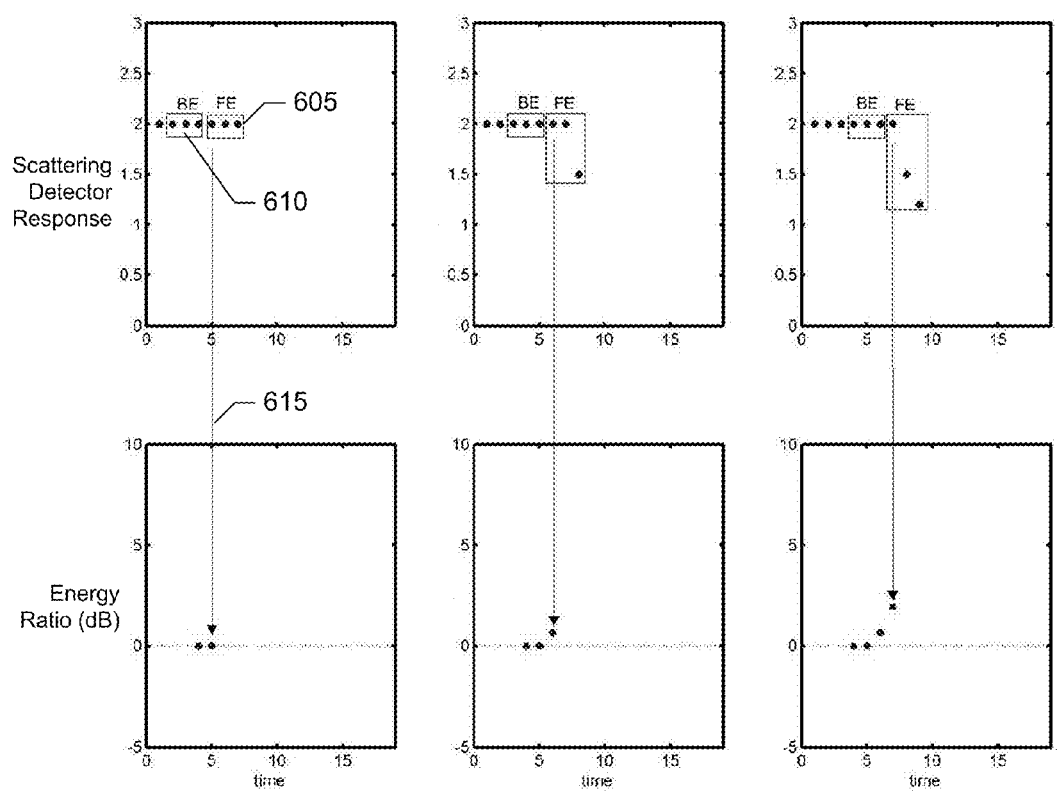
FIGS. 6A-6C depict example energy ratio computations according to one or more aspects of the present disclosure.
Figure 7A:
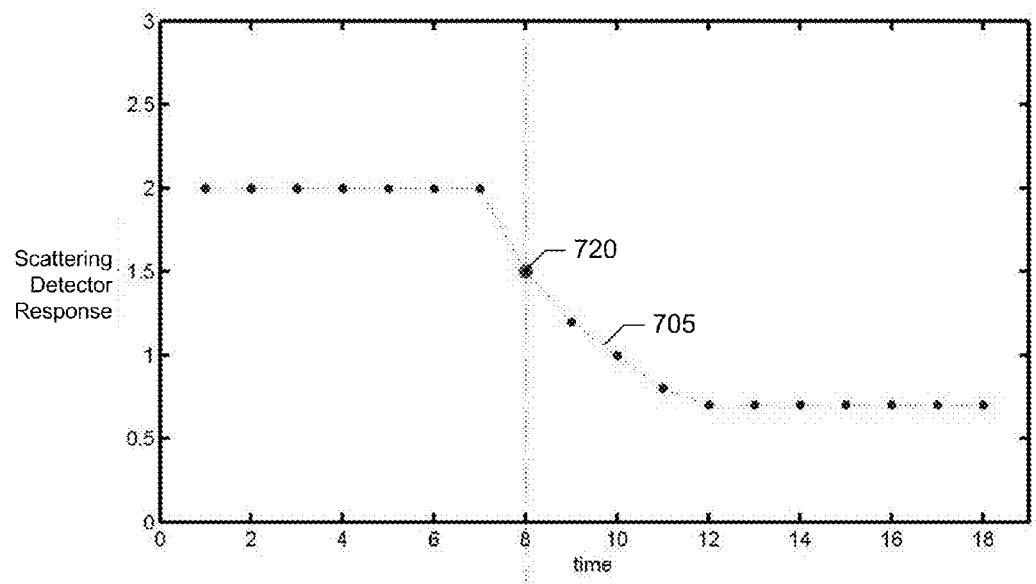
FIGS. 7A and 7B depict example energy ratios for the example fluids of FIGS. 5A and 5B.
Figure 7B:
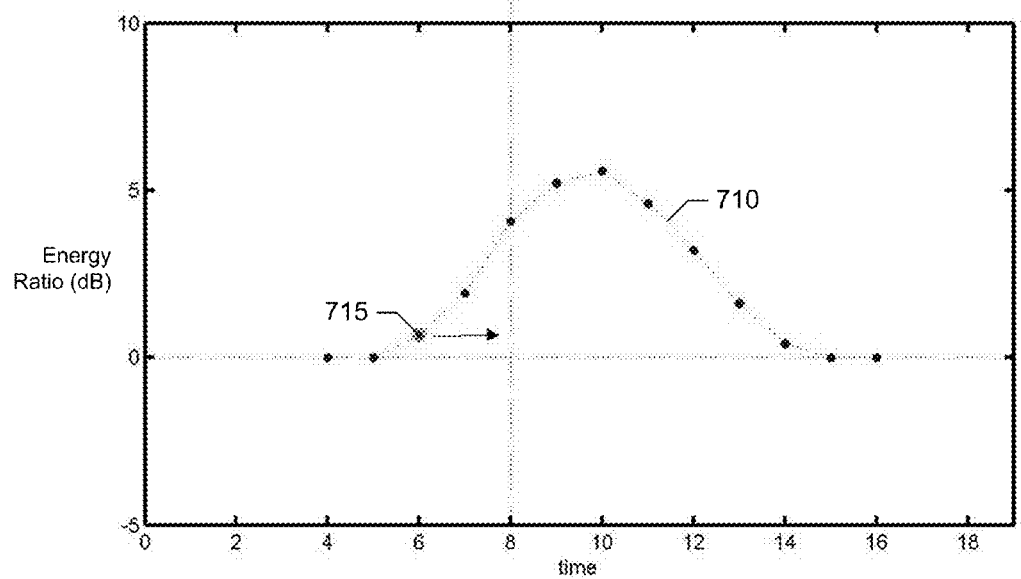

FIGS. 6A-6C and FIGS. 7A-7B depict an example computation of the energy ratio $e_i$ described above. FIG. 7A depicts an example scattering detector response 705 with FIG. 7B depicting a corresponding computed energy ratio 710. In the example of FIG. 7B, the size of window w is set equal to 3. FIGS. 6A-6C depict the step-by-step calculation of the example energy ratio 710 of FIG. 7B around the onset of phase-change. In FIG. 6A, the FE and BE windows are depicted as respective boxes 605 and 610 in the top subplot, and the computed energy ratio $e_i$ based on the computed FE and BE is registered in the bottom subplot at the corresponding time index, as shown by an arrow 615. FIGS. 6B and 6C show the subsequent scattering detector response and the corresponding energy ratios at subsequent time indices.

Returning to FIGS. 7A and 7B, the phase-change onset may be detected by identifying the data point 715 corresponding to when the energy ratio $e_i$ 710 exceeds a detection threshold. As described above, the increase in the energy ratio $e_i$ 710 is caused by the drop of scattering detector response 705 in the FE window and, therefore, the proper registration of phase-change onset corresponds to data point 720 in FIG. 7A, which is shifted to the right by w−1 (i.e., the window size w less one) from the detection of onset at point 715 of FIG. 7B.

The detection threshold may be selected as a small fixed value. In the examples described herein a threshold of 0.05 was used. Alternatively, the detected threshold may be selected based on a running statistic computed during (de-)pressurization. For example, a running standard deviation $\delta_i$ of the energy ratio $e_i$ may be computed as $$\delta_i = \sqrt{v_i - m_i^2}, \quad \text{EQN (4)}$$

where $$v_i = \frac{1}{i}\sum_{k=1}^{k=i} e_k^2, \quad \text{EQN (5)}$$

$$m_i = \frac{1}{i}\sum_{k=1}^{k=i} e_k, \quad \text{EQN (6)}$$

and i is the number of samples used to compute the statistic in EQNS (4)-(6). Note that example expressions of EQNS (5) and (6) may be computed recursively using the following mathematical expressions:

$$v_i = \frac{i-1}{i}v_{i-1} + \frac{1}{i}e_i^2, \text{ and} \quad \text{EQN (7)}$$

$$m_i = \frac{i-1}{i}m_{i-1} + \frac{1}{i}e_i. \quad \text{EQN (8)}$$

The time-varying detection threshold may be set equal to three times the standard deviation $\delta_i$ at each time index i after, for example, at least 10 samples of the energy ratio $e_i$ are available for computing the statistic. Alternatively, as described above, a fixed detection threshold may be used.

Measurements from other sensors of the example flowline 408 (e.g., the example P/T sensor 428 and/or the DV sensor 448) and/or other properties and/or quantities derived from these measurements may be used by the processor 470 to validate, confirm and/or quality check phase-change pressures determined based on light transmittances measured by the example SD 444.

Figure 8:
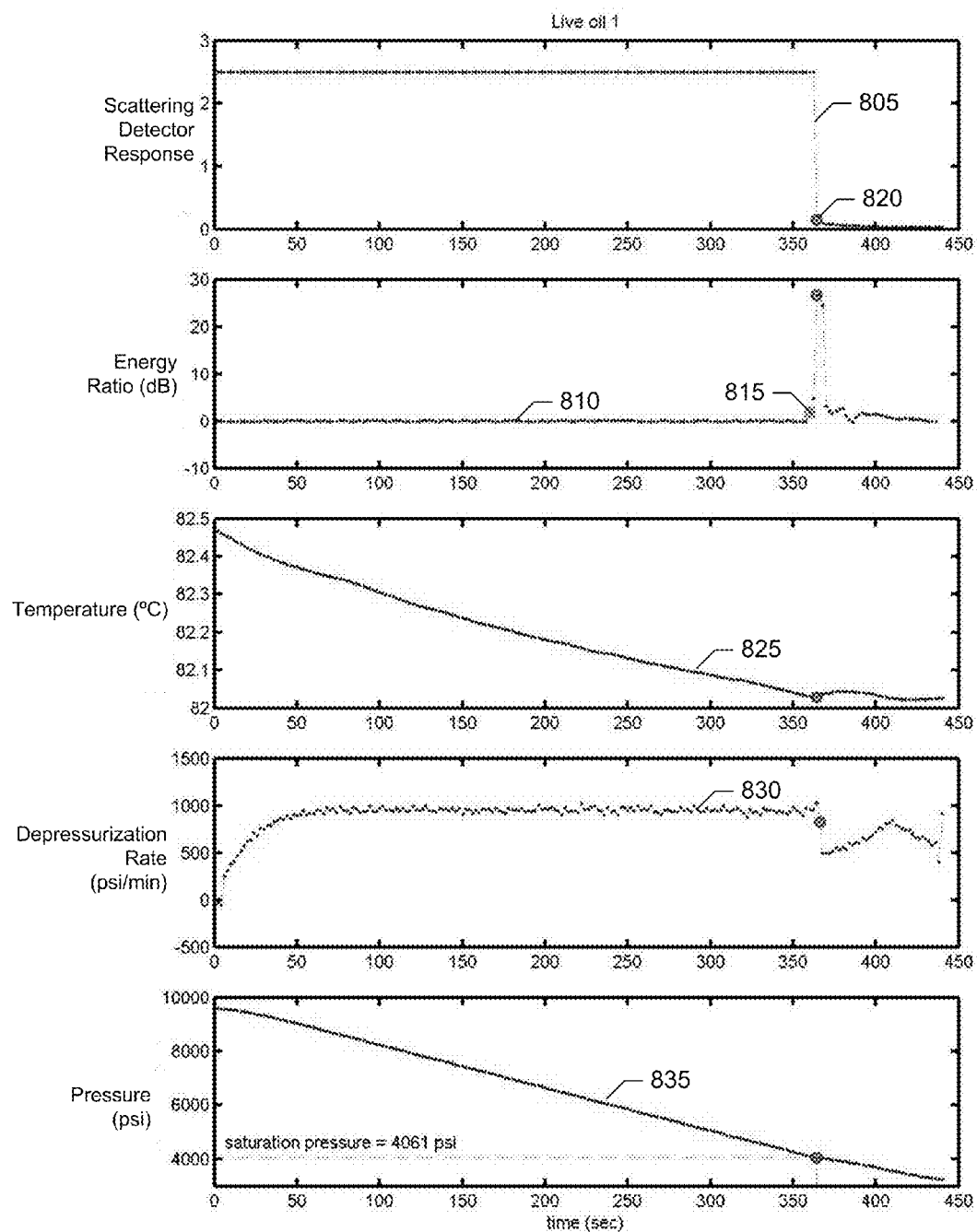
FIGS. 8-15 depict example measurements of different example fluids.

FIG. 8 depicts graphs of example measurements taken while the example live oil 1 of FIG. 5C is undergoing depressurization. The top two subplots are the scattering detector response 805 and the corresponding computed energy ratio 810, respectively. A point 815 on the computed energy ratio graph 810 corresponds to the energy ratio $e_i$ that exceeds the detection threshold and, therefore, may be used to identify the onset of phase-change at point 820, which may be identified by shifting to the right from the identified point 815 by w−1, wherein w is the size w of the FE and BE windows. In the example of FIG. 8, gas bubbles emerge when the onset of phase-change, which in the example of FIG. 8 is the bubble point, is reached.

A third subplot in FIG. 8 depicts example temperature readings 825 measured by the P/T sensor 428. As shown in FIG. 8, a decreasing trend in temperature 825 may occur during depressurization. However, at the onset of phase-change when the gas bubbles emerge, the temperature 825 may reverse its trend, as shown in FIG. 8. Therefore, temperature measurements 825 taken during depressurization may be used by the example processor 470 to corroborate and/or validate the detected phase-change 820.

A fourth subplot in FIG. 8 represents the depressurization rate 830 in psi/min, as computed and/or derived by the example controller 420. In the example of FIG. 8, the planned and/or intended depressurization rate is 1000 psi/min. However, as shown in FIG. 8, at the onset of phase-change, the actual depressurization rate 830 may deviate from the planned rate of 1000 psi/min. This is because, when the gas bubbles emerge at the onset of bubble point, the pressure reduction 830 of the fluid may become slower than before and the controller 420 may not immediately be able to compensate for this abrupt change in fluid properties. Therefore, a depressurization signature comprising an abrupt and/or unexpected reduction of the depressurization rate 830 from the planned value may be used by the processor 470 to confirm the onset of phase-change.

The bottom subplot of FIG. 8 depicts pressures 835 measured by the example P/T sensor 428 during the depressurization. The measured pressures 835 at the time corresponding to the detected phase-change onset corresponds to the phase-change pressure. The phase-change pressure identified in FIG. 8 is 4061 psi, which agrees well with $P_b$ of 4060 psi measured using a constant composition expansion (CCE) procedure performed in a laboratory. Note that the pressure versus time profile 835 of FIG. 8 is nearly linear without distinct features, making the detection of phase-change pressure from this pressure profile 835 difficult and/or less reliable.

Figure 9:
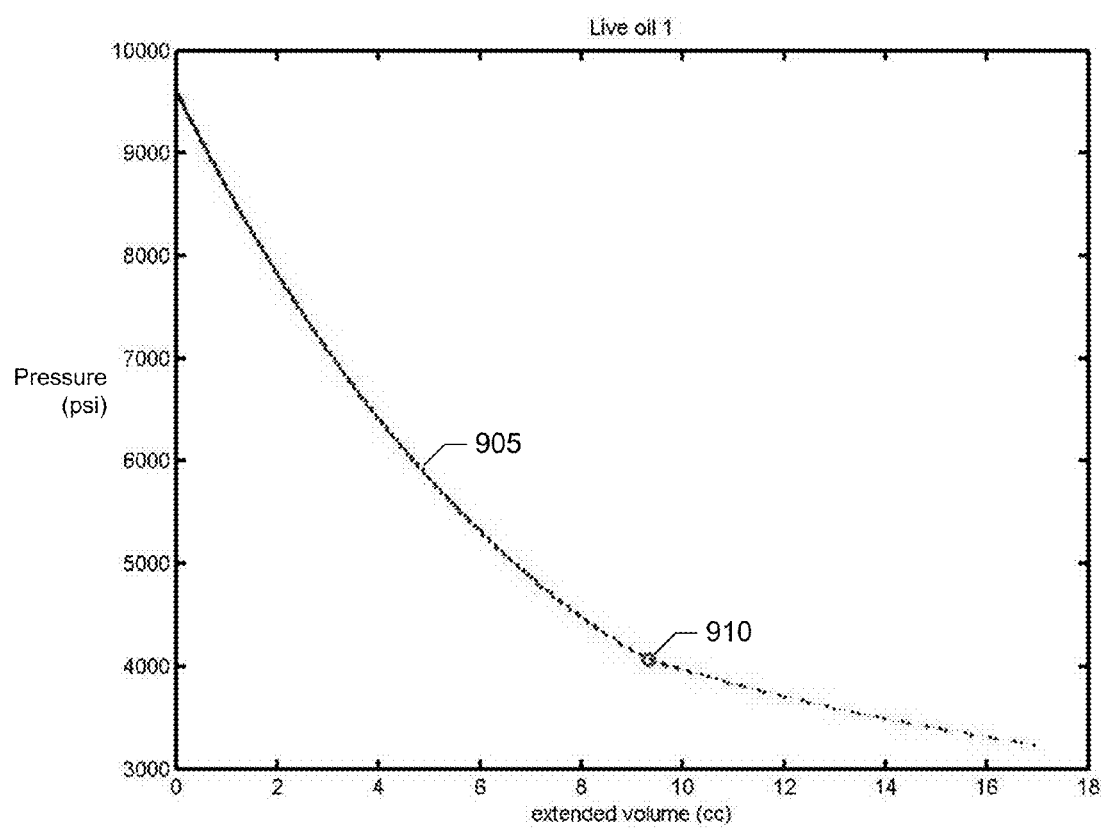

FIG. 9 depicts a graph of pressures 905 versus the extended volume (i.e., PV data) for the example depressurization of live oil 1 depicted in FIG. 8. The example data 905 of FIG. 9 shows a smooth transition around the onset 910 of phase-change, which may make a reliable and/or accurate detection of the phase-change pressure based on the example PV data 905 difficult. However, for some fluids PV data may be used by the processor 470 to confirm and/or corroborate the detection of the onset of phase-change.

Figure 10:
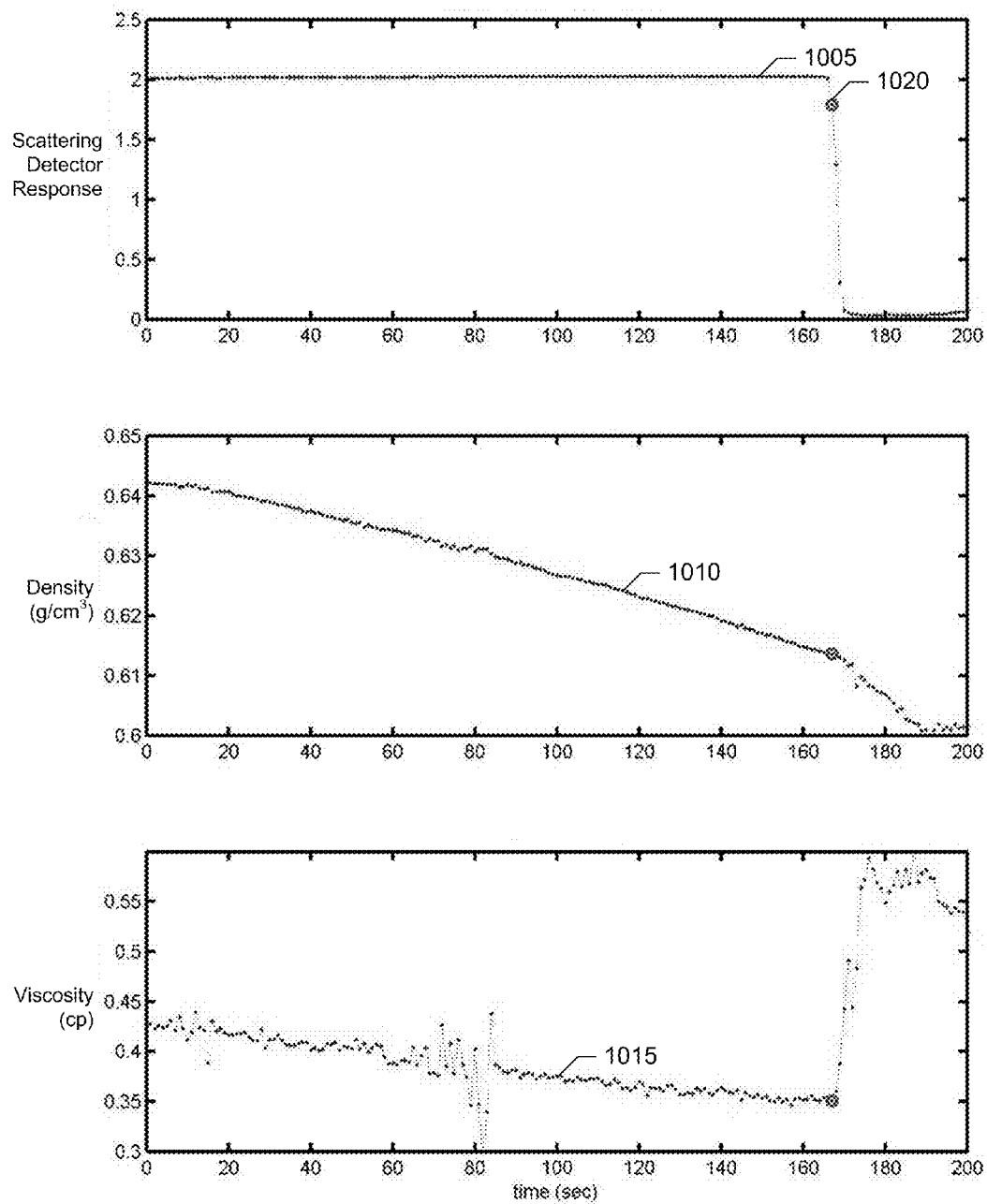

The fluid densities and/or viscosities measured by the example DV sensor 448 during depressurization may, additionally or alternatively, be used to validate, confirm and/or quality control the phase-change pressures determined from light transmittances. FIG. 10 shows example SD responses 1005, example densities 1010 and example viscosities 1015 measured for a volatile oil during depressurization without circulation. A point 1020 in the top subplot of FIG. 10 corresponds to the onset of phase-change (e.g., bubble point) detecting using the energy ratio $e_i$ described above. While the measured fluid is still in single phase, the fluid densities 1010 and the fluid viscosities 1015 exhibit a generally linearly decreasing trend with decreasing pressure. Once the onset 1020 of phase-change is reached, gas bubbles emerge and the fluid densities 1010 and the fluid viscosities 1015 in the two-phase fluid may abruptly deviate from the single-phase trend as shown in FIG. 10. These deviations of the densities 1010 and/or the viscosities 1015 from the single-phase trend may, therefore, be used by the example processor 470 to confirm the detected phase-change 1020.

FIGS. 11-16 illustrate example sensor measurements and energy ratios, as described above in connection with FIG. 8, for other example fluids. As shown in the examples of FIGS. 11-16, the example methods and apparatus to determine phase-change pressures disclosed herein are applicable to any number and/or type(s) of fluids.

Figure 11:
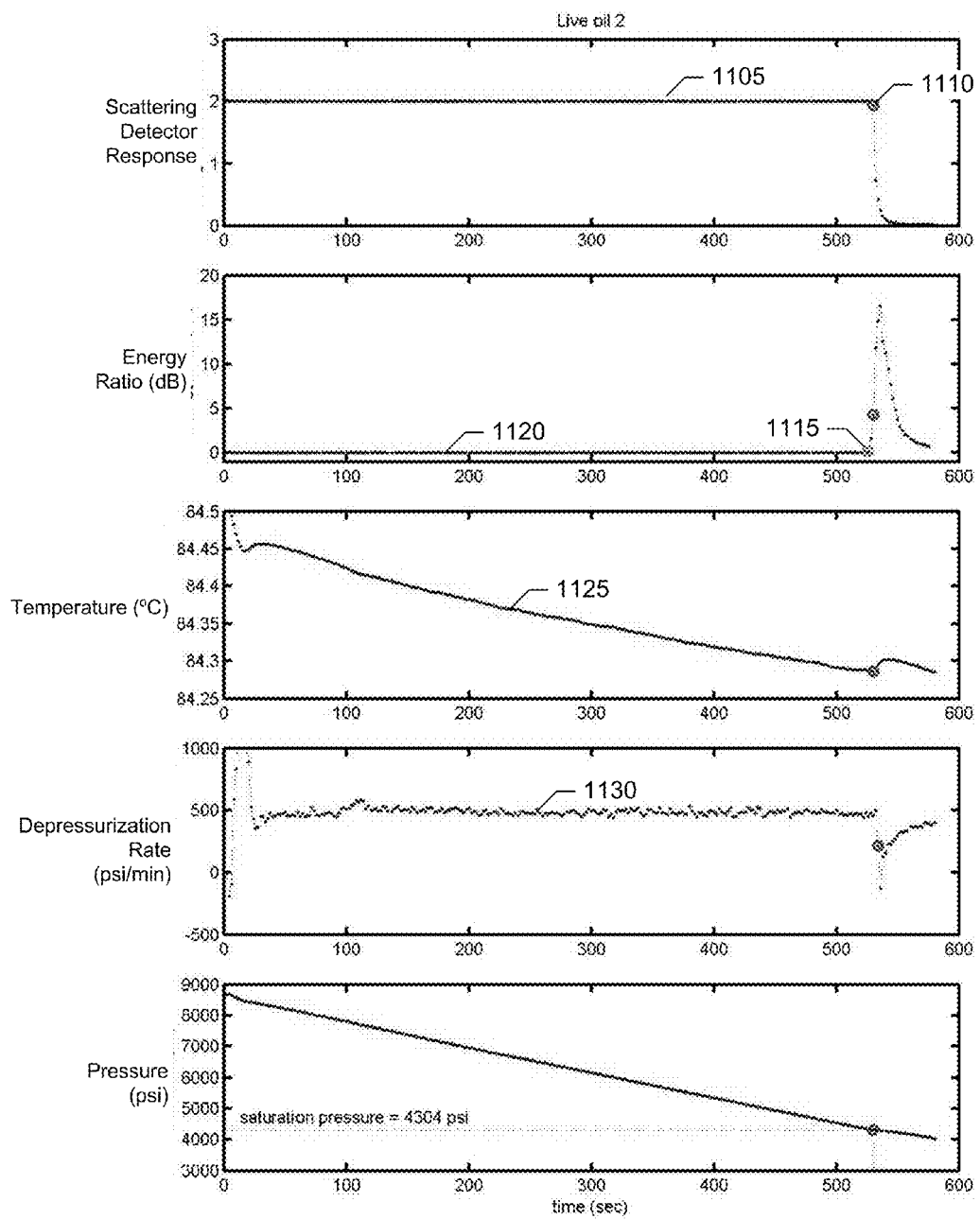

In FIG. 11, the example live oil 2 of FIG. 5C has been depressurized. Unlike the example of FIG. 8, the scattering detector response 1105 decreases gradually at and after the onset of phase-change. However, the example methods and apparatus described herein correctly identify the onset of phase-change and the corresponding phase-change pressure 1110 (saturation pressure). As discussed above, a point 1115 on the computed energy ratio curve 1120 corresponds to when the energy ratio 1120 exceeds the detection threshold. Furthermore, the temperature measurements 1125 and the depressurization rates 1130 corroborate the detected onset of phase-change.

Figure 12:
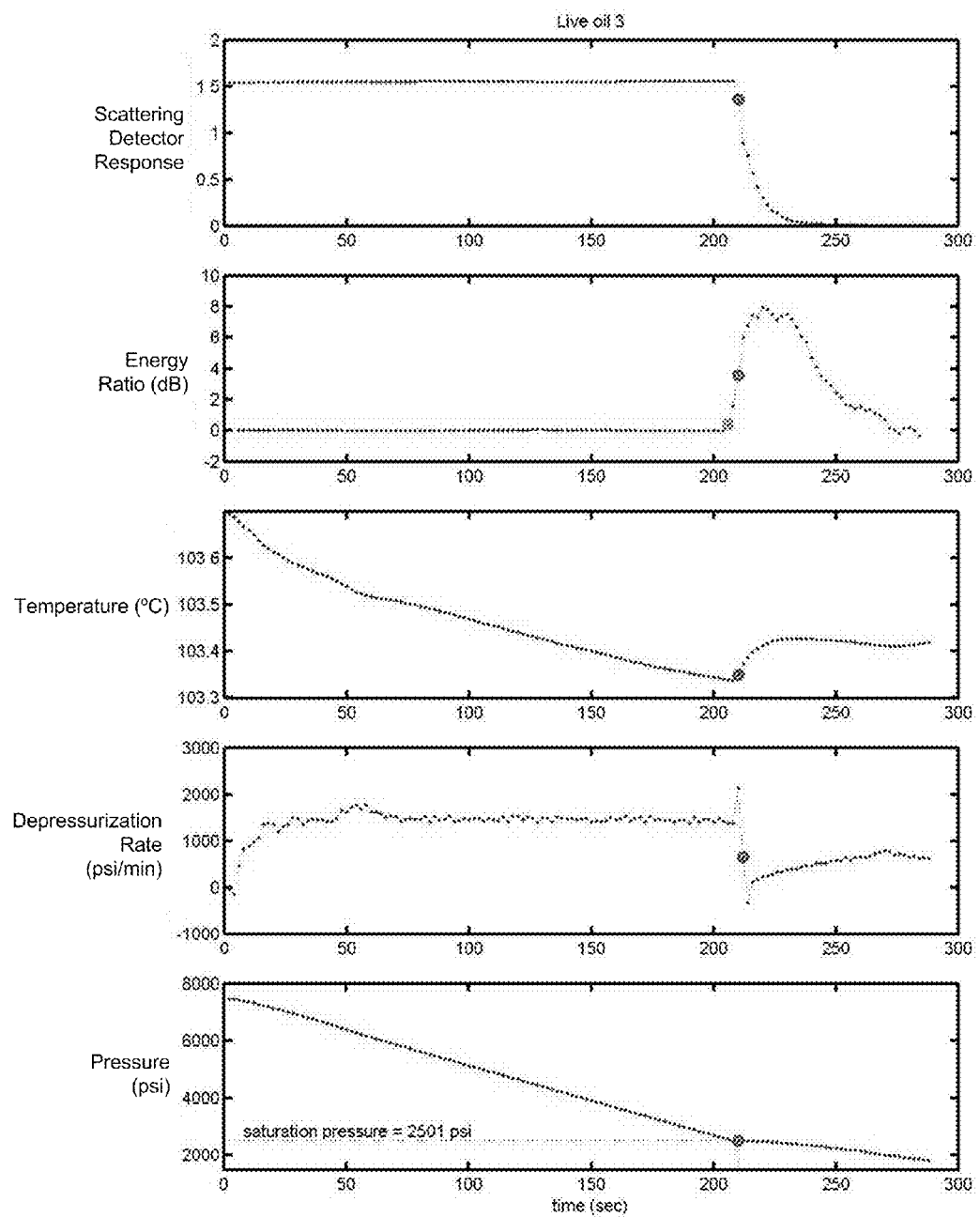

FIG. 12 shows the results for the example live oil 3 of FIG. 5C. In the illustrated example of FIG. 12, the fluid undergoes a faster depressurization at a rate of 1500 psi/min. The detected onset of phase-change using the methods and apparatus described herein is consistent with the reverse trend in temperature measurement and the signature drop in the depressurization rate at the phase-change onset. The detected saturation pressure in FIG. 12 is 2501 psi, which is in agreement with the CCE $P_b$ of 2543 psi measured in a laboratory.

Figure 13:
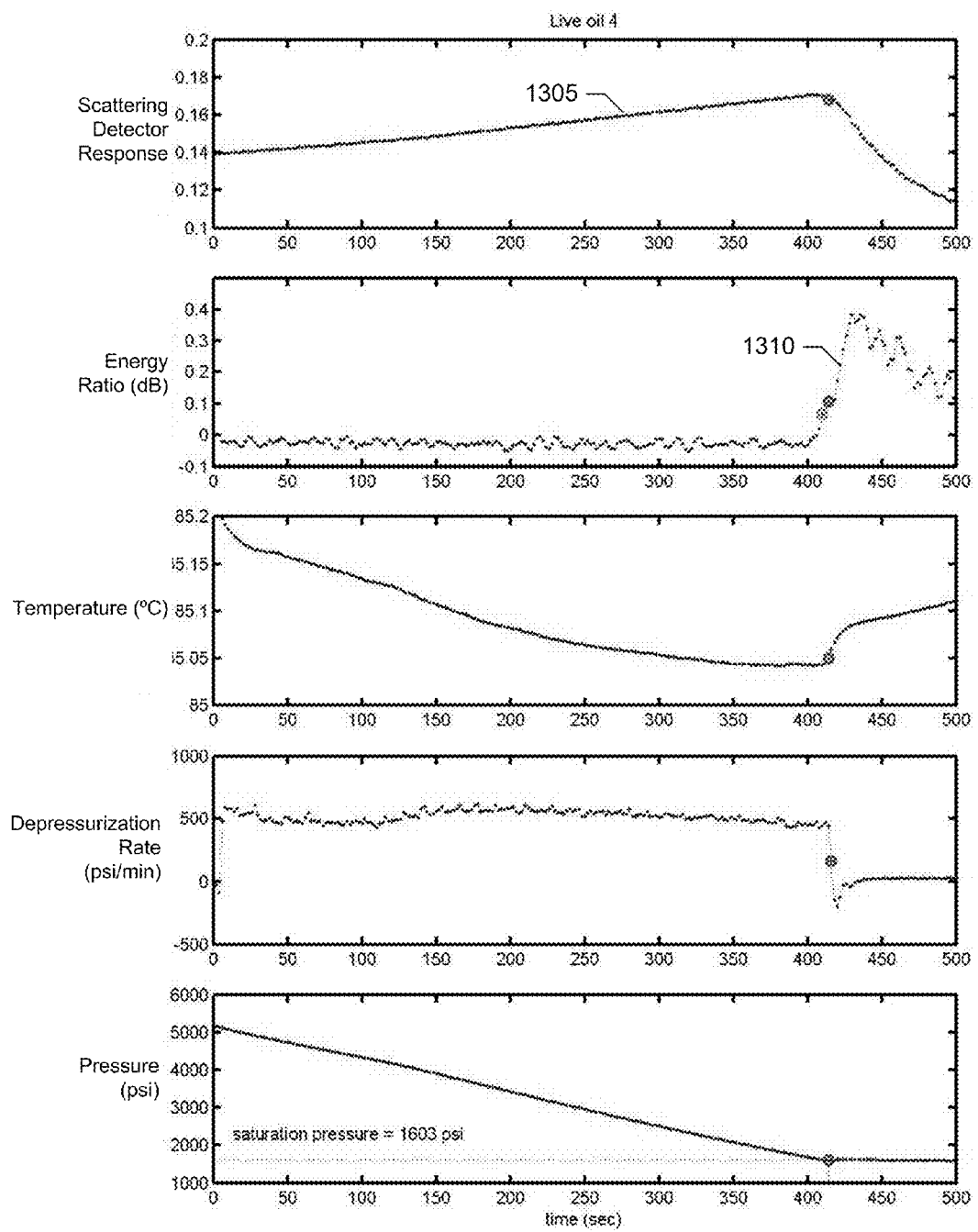

FIG. 13 shows example results for the example live oil 4 of FIG. 5C. Live oil 4 is very dark in color and is the most viscous among all example fluids shown in FIG. 5C. From the scattering detector response 1305 shown in the top subplot of FIG. 13, the light transmission through live oil 4 is weaker in comparison with the examples discussed above, but the light transmittance is still measurable. Before reaching the onset of phase-change, the scattering detector response 1305 increases slightly as the pressure decreases, which is caused by the combined effect of color absorption and fluid density as explained above. The computed energy ratio 1310 is predominately less than zero before the onset is reached. At the scale that the computed energy ratio 1310 is shown in FIG. 13, the fluctuations in the computed energy ratio 1310 represent noise in the scattering detector data 1305. The onset of phase-change is detected at 1603 psi in agreement with CCE $P_b$ of 1550 psi. The detected onset is further corroborated and confirmed by the reverse temperature trend and the signature drop in the depressurization rate that occurred at the onset of phase-change. In the example of FIG. 13, the pressure versus time profile shown in the bottom subplot changes at the phase-change pressure, which may also be used to corroborate and/or confirm the detected onset of phase-change.

Figure 14:
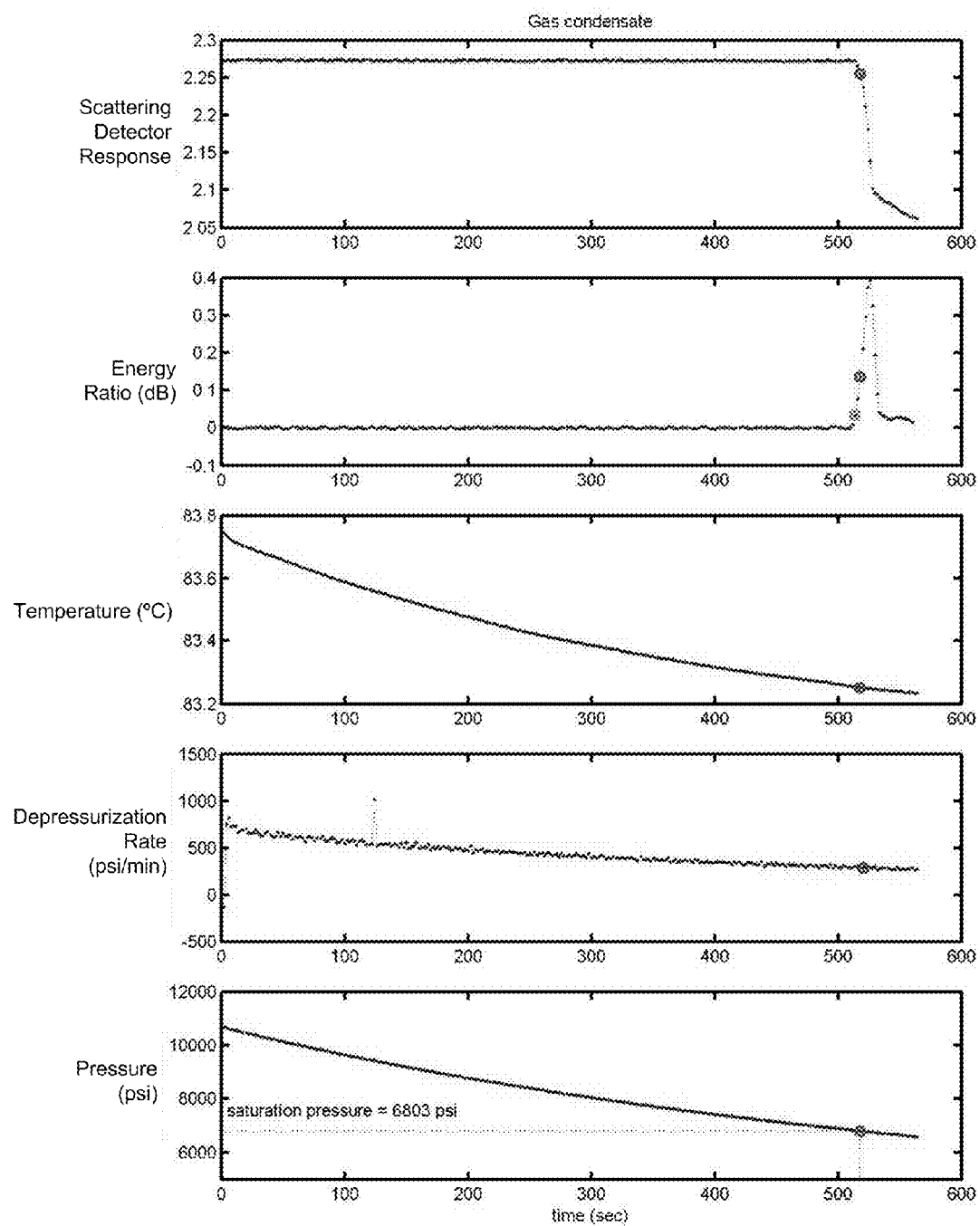

FIG. 14 shows example results for the example gas condensate of FIG. 5C. In this example, liquid droplets emerge when the onset of phase-change is reached. As shown, the onset of phase-change may be detected using the example methods and apparatus disclosed herein. The detected saturation pressure (i.e., dew point pressure in this case) is 6808 psi, which again is in a good agreement with the CCE $P_d$ of 6760 psi measured in a laboratory. However, the reverse trend in temperature reading and the signature drop in the depressurization rate at the phase-change onset are not apparent for gas condensate, as shown in FIG. 14. The lack of correlation of temperature reading and/or depressurization rate with the onset of phase-change may be used to perform, for example, fluid identification (i.e. gas condensate vs. live oil) when combined with other measurements.

Figure 15:
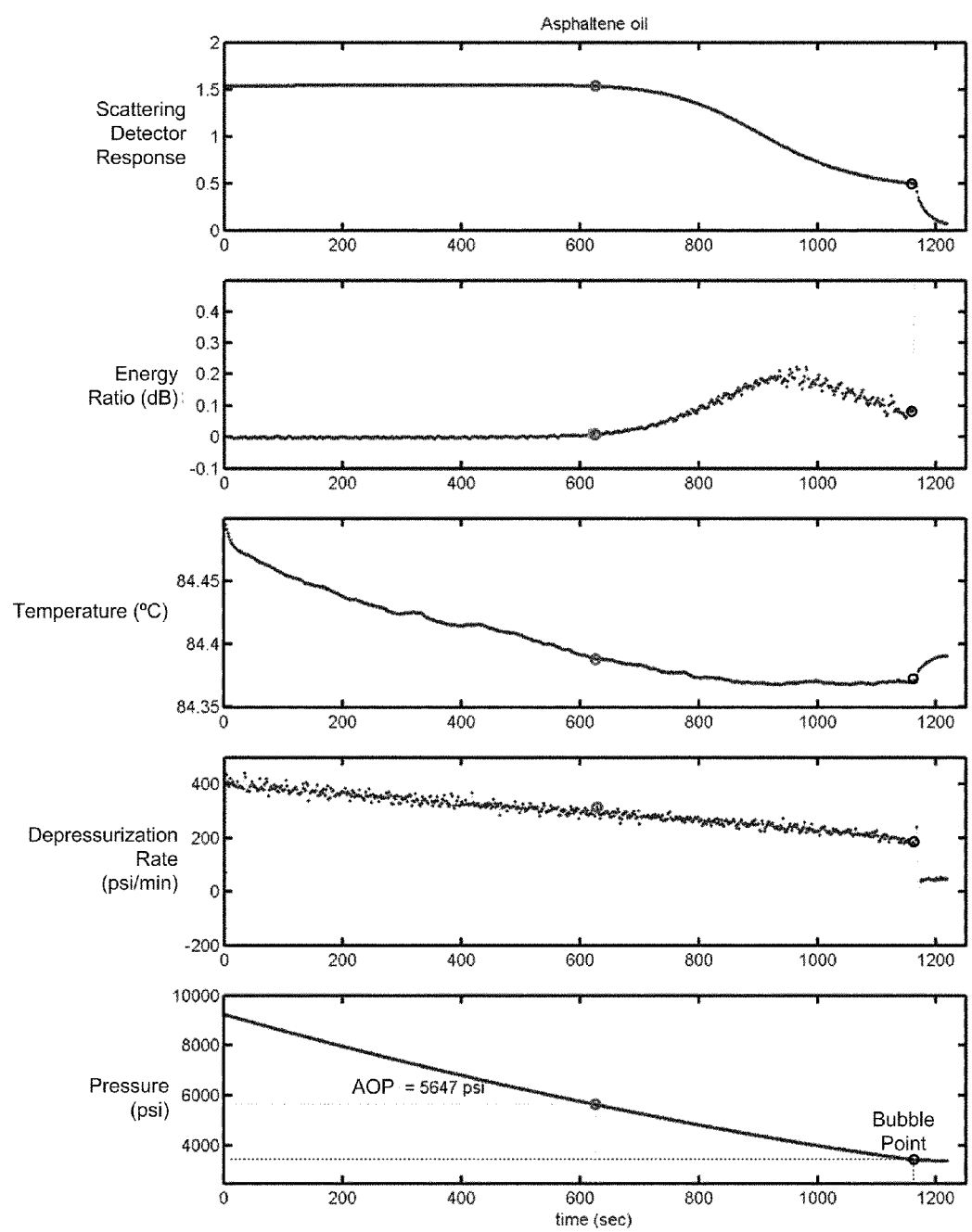

FIG. 15 shows example results for the example asphaltene live oil of FIG. 5C. For asphaltene oil, there are typically two onsets corresponding to different fluid phase-changes. The first occurs at a higher onset pressure where the asphaltene particulates precipitate whereas the second happens at a lower onset pressure where the gas bubbles emerge from fluid. The former is called the AOP and the latter is the bubble point pressure. It may be useful to be able to identify the presence of asphaltene and its onset in situ. Depending on the composition of formation fluid the presence of AOP may or may not occur during depressurization. One method that may be used to identify the presence of AOP is to measure the colloidal instability index of reservoir fluid. However, methods to measure the colloidal instability index may not be applicable for downhole applications. As shown in FIG. 15, the methods and apparatus described herein may be used downhole to detect the asphaltene onset in situ. To identify whether an observed reduction in light transmittance is caused by asphaltene precipitation or emerging gas bubbles, the other example measurements depicted in FIG. 15 may be used to delineate the occurrence of AOP. As shown in FIG. 15, asphaltene precipitation causes a reduction of light transmission but does not coincide with a reversal of the temperature trend or the signature drop in the depressurization rate. Additionally or alternatively, a GOR of the fluid determined using the example SP 464 may be used to distinguish asphaltene live oil from gas condensate and thereby identify the presence of AOP, even though the dew point of gas condensate may show similar sensor responses, as discussed above in connection with FIG. 14. When the gas bubbles finally emerge at a lower onset pressure (around 1150 seconds in FIG. 15), an additional drop in the scattering detector response accompanied by the reverse trend in temperature reading and the signature drop in the depressurization rate may be used by the example processor 470 to detect the onset of bubble point. As shown in FIG. 15, the example methods and apparatus described herein may be used to identify and/or detect both AOP and bubble point pressure, without having to measure the colloidal instability index of fluid in a laboratory.

While an example fluid isolation and analysis tool 126 that may be used to determine phase-change pressures and/or detect phase-change onset is shown in FIGS. 4A-C, one or more of the elements, sensors, circuits, modules, processors, controllers and/or devices illustrated in FIGS. 4A-C may be combined, divided, re-arranged, omitted, eliminated and/or implemented in any other way. Further, any of the example elements, sensors, circuits, modules, processors, controllers, devices and/or more generally the example fluid isolation and analysis tool 126 of FIGS. 1-3 and 4A-4C may be implemented by hardware, software, firmware and/or any combination of hardware, software and/or firmware. Thus, for example, any or all of the example elements, sensors, circuits, modules, processors, controllers, devices and/or more generally the example fluid isolation and analysis tool 126 may be implemented by one or more circuit(s), programmable processor(s), application specific integrated circuit(s) (ASIC(s)), programmable logic device(s) (PLD(s)), field-programmable logic device(s) (FPLD(s)), field-programmable gate array(s) (FPGA(s)), etc. Further still, the fluid isolation and analysis tool 126 may include elements, sensors, circuits, modules, processors, controllers and/or devices instead of or in addition to those illustrated in FIGS. 4A-C, and/or may include more than one of any or all of the illustrated elements, sensors, circuits, modules, processors, controllers and/or devices.

Figure 16A:
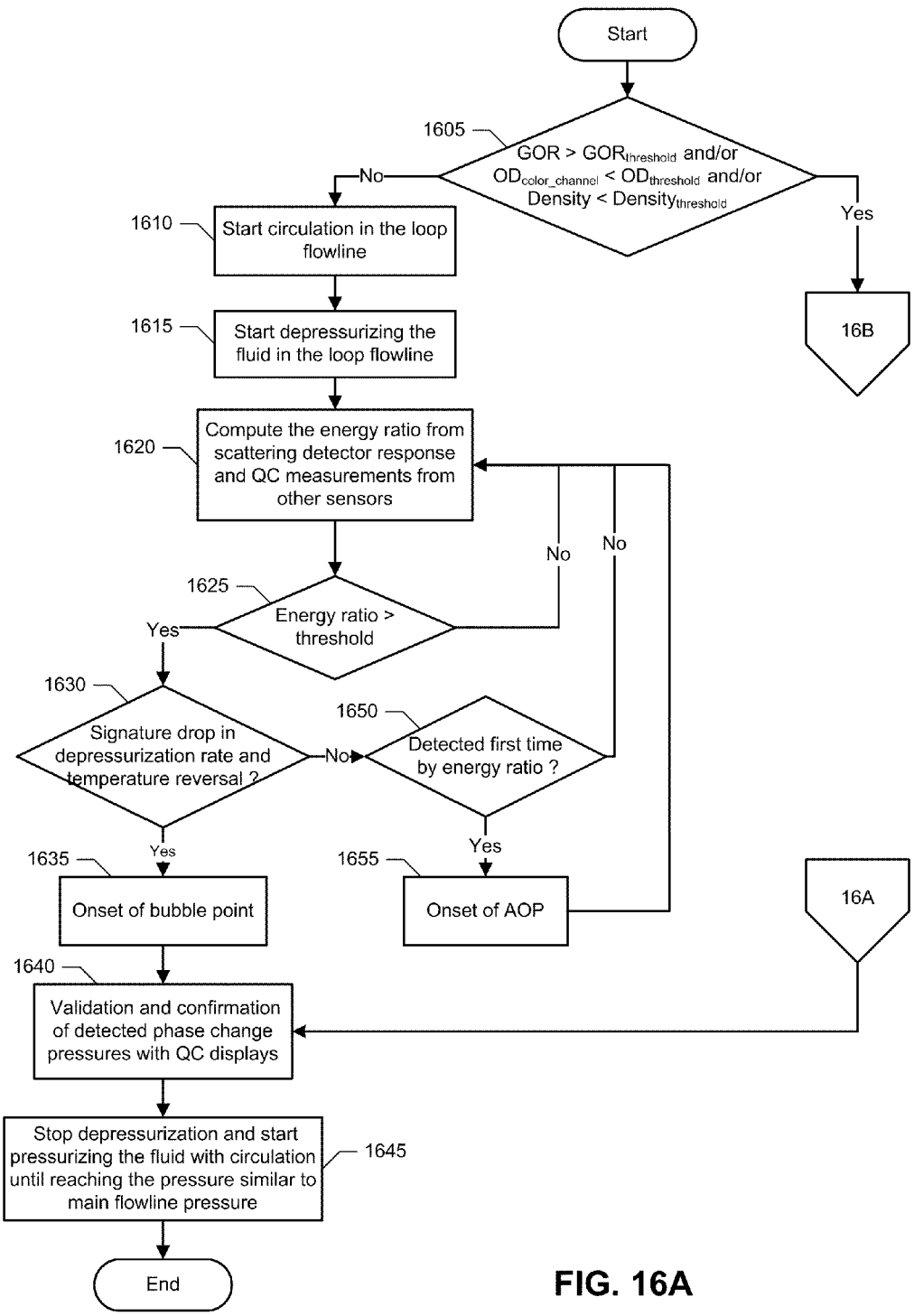
FIGS. 16A and 16B depict an example process according to one or more aspects of the present disclosure.

FIGS. 16A and 16A are a flowchart representative of an example process that may be carried out to implement the example fluid isolation and analysis tool 126 of FIGS. 1-3 and 4A-4C. The example process of FIGS. 16A and 16A may be carried out by a processor, a controller and/or any other suitable processing device. For example, the example process of FIGS. 16A and 16A may be embodied in coded instructions stored on an article of manufacture such as any tangible computer-readable and/or computer-accessible media. Example tangible computer-readable medium include, but are not limited to, a flash memory, a compact disc (CD), a digital versatile disc (DVD), a floppy disk, a read-only memory (ROM), a random-access memory (RAM), a programmable ROM (PROM), an electronically-programmable ROM (EPROM), and/or an electronically-erasable PROM (EEPROM), an optical storage disk, an optical storage device, magnetic storage disk, a magnetic storage device, and/or any other tangible medium which can be used to store and/or carry program code and/or instructions in the form of machine-accessible and/or machine-readable instructions or data structures, and which can be accessed by a processor, a general-purpose or special-purpose computer, or other machine with a processor (e.g., the example processor 470 of FIG. 4A and/or the example processor platform P100 discussed below in connection with FIG. 17). Combinations of the above are also included within the scope of computer-readable media. Machine-readable instructions comprise, for example, instructions and/or data that cause a processor, a general-purpose computer, special-purpose computer, or a special-purpose processing machine to implement one or more particular processes. Alternatively, some or all of the example process of FIGS. 16A and 16A may be implemented using any combination(s) of ASIC(s), PLD(s), FPLD(s), FPGA(s), discrete logic, hardware, firmware, etc. Also, some or all of the example process of FIGS. 16A and 16A may instead be implemented manually or as any combination of any of the foregoing techniques, for example, any combination of firmware, software, discrete logic and/or hardware. Further, many other methods of implementing the example operations of FIGS. 16A and 16A may be employed. For example, the order of execution of the blocks may be changed, and/or one or more of the blocks described may be changed, eliminated, sub-divided, or combined. Additionally, any or all of the example process of FIGS. 16A and 16A may be carried out sequentially and/or carried out in parallel by, for example, separate processing threads, processors, devices, discrete logic, circuits, etc.

Figure 16B:
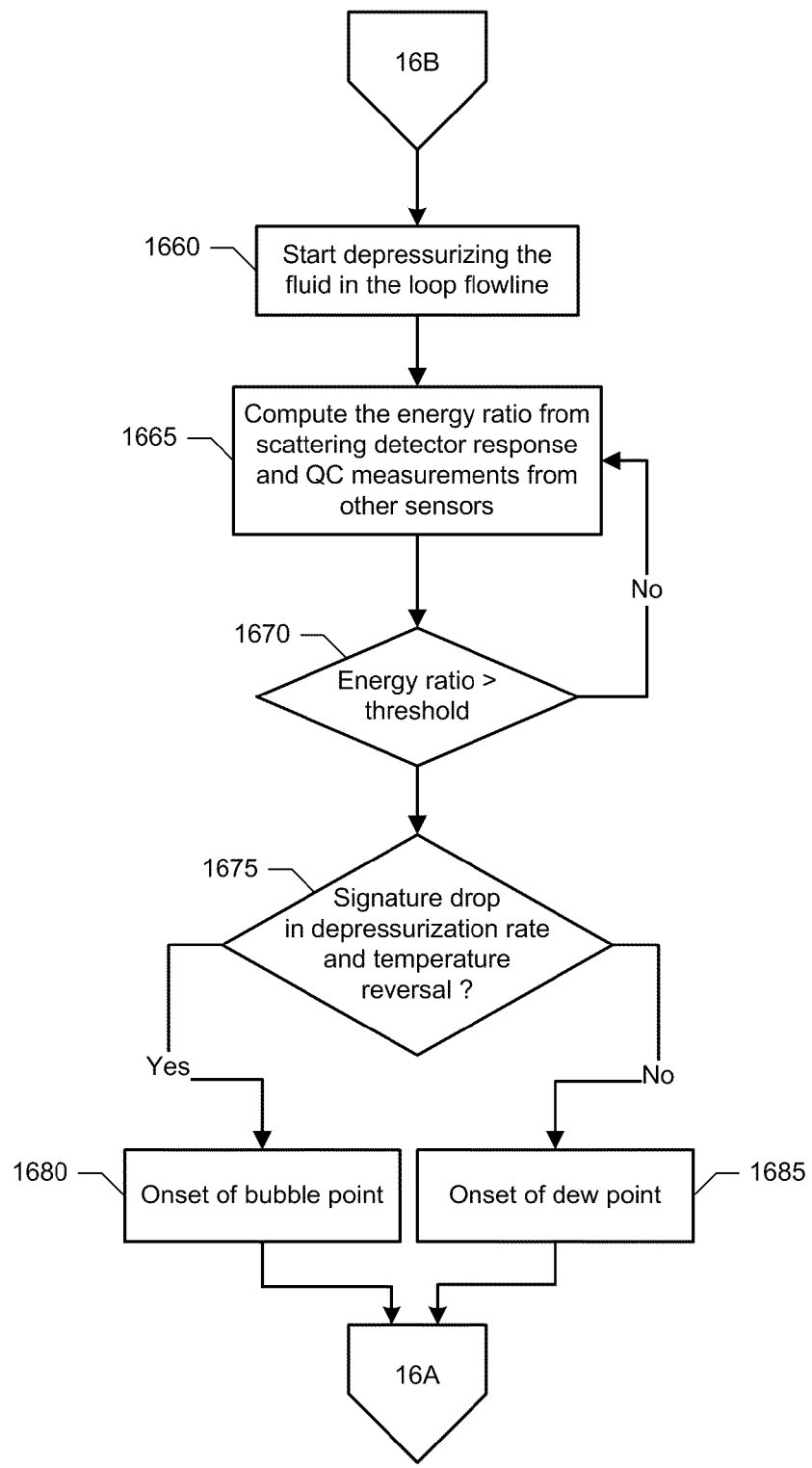

The example process of FIGS. 16A and 16B begins with the example processor 470 comparing one or more of a GOR value measured by the example SP 464, an optical density (OD) value and/or a fluid density value to respective thresholds to identify and/or determine a fluid type (block 1605). For example, a GOR threshold of 3300 standard cubic feet per stock tank barrel (scf/stb) may be used to separate crude oil from gas condensate. The separation of fluid type may be used to determine whether circulation of the fluid by the CP 452 is required during depressurization. Additionally or alternatively, the OD in the visible and/or near-infrared region may be measured by the SP 464 and used to identify the fluid type. For example, crude oil typically exhibits some coloration while gas condensate is nearly colorless. This is particularly true for crude oil containing asphaltenes which may contribute significant color absorption. Accordingly, one may set a low OD threshold of, for example, 0.1 for the identification of fluid type. Further still, one can also include the density of fluid measured by the DV sensor 460, 448 to identify the fluid type. The density threshold, for example, can be set at 0.4 grams per cubic centimeter (g/cm$^3$) to roughly separate crude oil from gas condensate.

If a crude oil is identified at block 1605, circulation of the fluid in the flowline 408 by the CP 452 is started (block 1610), and the controller 420 begins systematically depressurization of the fluid (block 1615). As the fluid is depressurized, the example processor 470 computes the example energy ratio $e_i$ from the light transmittances measured by the example SD 444 (block 1620).

If the energy ratio $e_i$ does not exceed the detection threshold (block 1625), control returns to block 1620 to continue computing energy ratio values. When the energy ratio $e_i$ exceeds the detection threshold (block 1625), the processor 470 determines whether the temperatures measured by the P/T sensor 428 exhibit a temperature reversal and the pressurization rates computed by the controller 420 exhibit a signature drop (block 1630).

If the temperature reversal and/or the pressurization rate drop are found (block 1630), the onset of bubble pressure has been detected (block 1635). The onset of bubble pressure may be validated, collaborated and/or quality checked using other measurements such as density and/or viscosity (block 1640), as described above in connection with FIG. 10. While the example DV sensor 448 is more accurate when the fluid in the test flowline 408 is not moving or flowing during measurement of the densities and/or viscosities, other DV sensors that work accurately and/or reliably in the presence of a vibrating fluid pump may be implemented. Depressurization of the fluid is discontinued and the fluid is re-pressurized to a pressure substantially equal to the pressure of the main flowline 440 (block 1645). Control then exits from the example process of FIGS. 16A and 16B.

Returning to block 1630, if the temperature reversal and/or the pressurization rate drop did not occur (block 1630), and this is not the first time that the energy ratio $e_i$ exceeded the threshold (block 1650), control returns to block 1620. If this is the first time that the energy ratio $e_i$ exceeded the threshold (block 1650), then the onset of AOP has been detected (block 1655). Control then returns to block 1620 to detect the onset of bubble point.

Returning to block 1605, if a crude oil has not been identified (block 1605), control proceeds to block 1660 of FIG. 16B. At block 1660 of FIG. 16B, the controller 420 begins systematically depressurizing the fluid without circulation. As the fluid is depressurized, the example processor 470 computes the example energy ratio $e_i$ from the light transmittances measured by the example SD 444 (block 1665).

If the energy ratio $e_i$ does not exceed the detection threshold (block 1670), control returns to block 1665 to continue computing energy ratio values. When the energy ratio $e_i$ exceeds the detection threshold (block 1670), the processor 470 determines whether the temperatures measured by the P/T sensor 428 exhibit at temperature reversal and the pressurization rates computed by the controller 420 exhibit a signature drop (block 1675).

If the temperature reversal and/or the pressurization rate drop are found (block 1675), the bubble point pressure has been detected (block 1680). Control then proceeds to block 1640 of FIG. 16A.

If the temperature reversal and/or the pressurization rate drop are not found (block 1675), the dew point pressure has been detected (block 1685). Control then proceeds to block 1640 of FIG. 16A.

Figure 17:
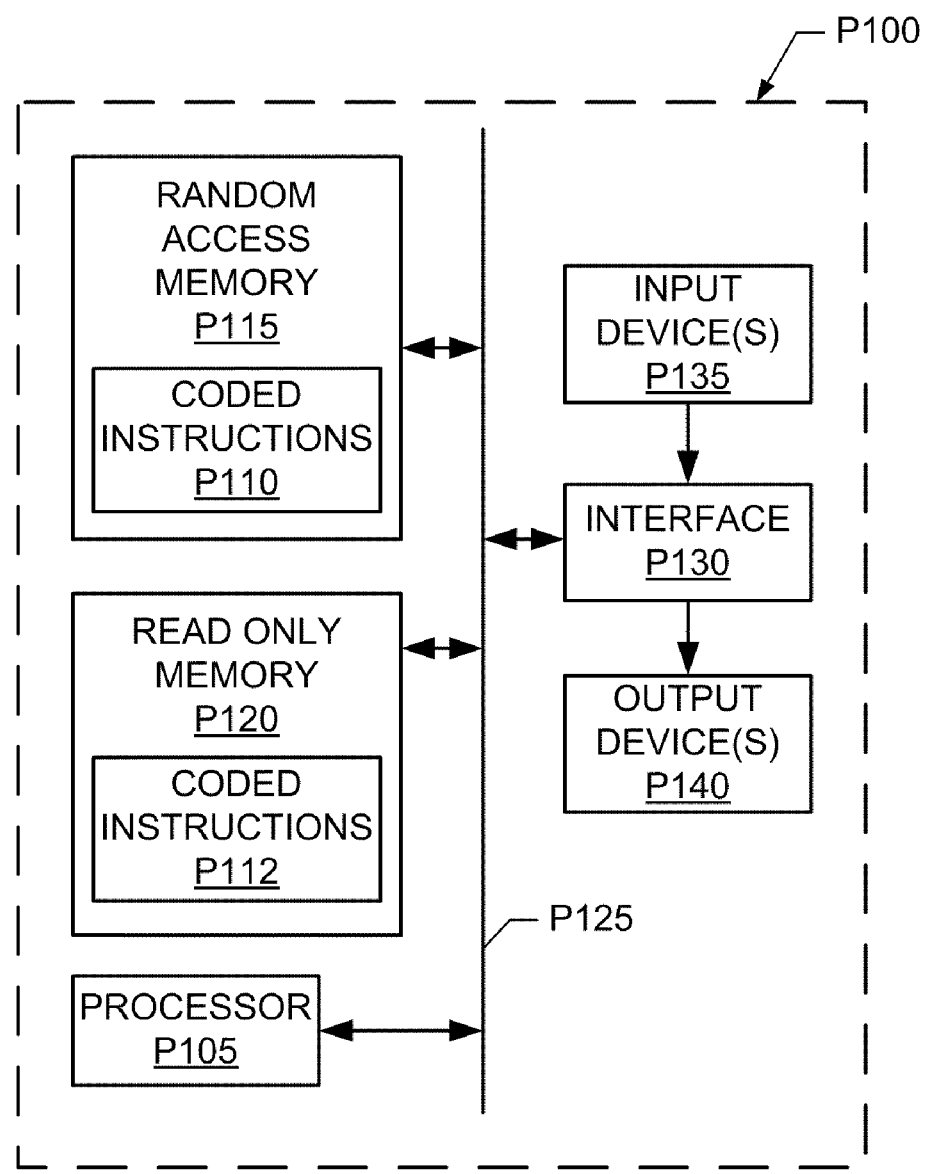
FIG. 17 depicts an example processor platform that may be used and/or programmed to implement one or more aspects of the present disclosure.

FIG. 17 is a schematic diagram of an example processor platform P100 that may be used and/or programmed to implement the example fluid isolation and analysis tool 126 of FIGS. 1-3, 4A-C and/or the example process of FIGS. 16A and 16B. For example, the processor platform P100 can be implemented by one or more general-purpose processors, processor cores, microcontrollers, etc.

The processor platform P100 of the example of FIG. 17 includes at least one general-purpose programmable processor P105. The processor P105 executes coded instructions P110 and/or P112 present in main memory of the processor P105 (e.g., within a RAM P115 and/or a ROM P120). The processor P105 may be any type of processing unit, such as a processor core, a processor and/or a microcontroller. The processor P105 may carry out, among other things, the example process of FIGS. 16A and 16B to determine phase-change pressures and/or detect phase-change onsets.

The processor P105 is in communication with the main memory (including a ROM P120 and/or the RAM P115) via a bus P125. The RAM P115 may be implemented by dynamic random-access memory (DRAM), synchronous dynamic random-access memory (SDRAM), and/or any other type of RAM device, and ROM may be implemented by flash memory and/or any other desired type of memory device. Access to the memory P115 and the memory P120 may be controlled by a memory controller (not shown). The memory P115, P120 may be used to implement the example storage 424 of FIG. 4A.

The processor platform P100 also includes an interface circuit P130. The interface circuit P130 may be implemented by any type of interface standard, such as an external memory interface, serial port, general-purpose input/output, etc. One or more input devices P135 and one or more output devices P140 are connected to the interface circuit P130. The example output device P140 may be used to, for example, control the example motor 416. The example input device P135 may be used to, for example, receive measurements from the example sensors 428, 444, 448, 456, 460 and/or 464.

In view of the foregoing description and the figures, it should be clear that the present disclosure introduces methods and apparatus to determine phase-change pressures. In particular, the present disclosure introduces methods including capturing a fluid in a chamber, (de-)pressurizing the fluid at a plurality of pressures, measuring a plurality of transmittances of a signal through the fluid at respective ones of the plurality of pressures, computing a first magnitude of a first subset of the plurality of transmittances, computing a second magnitude of a second subset of the plurality of transmittances, comparing the first and second magnitudes to determine a phase-change pressure for the fluid.

The present disclosure further introduces formation fluid analysis tools including a flowline, a valve configured to capture a fluid in the flowline, a pressure control unit configured to (de-)pressurize the fluid at a plurality of pressures, a scattering detector configured to measure a plurality of transmittances of a signal through the fluid at respective ones of the plurality of pressures, and a processor configured to compute a first magnitude of a first subset of the plurality of transmittances, compute a second magnitude of a second subset of the plurality of transmittances, comparing the first and second magnitudes to determine a phase-change pressure for the fluid.

Although certain example methods, apparatus and articles of manufacture have been described herein, the scope of coverage of this patent is not limited thereto. On the contrary, this patent covers all methods, apparatus and articles of manufacture fairly falling within the scope of the appended claims either literally or under the doctrine of equivalents.

What is claimed is:

1. A method, comprising:
   capturing a fluid in a chamber;
   pressurizing the fluid at a plurality of pressures;
   measuring a plurality of transmittances of a signal through the fluid at respective ones of the plurality of pressures;
   computing a first magnitude of a first subset of the plurality of transmittances;
   computing a second magnitude of a second subset of the plurality of transmittances; and comparing the first and second magnitudes to determine a phase-change pressure for the fluid.

2. The method of claim 1 wherein the signal comprises an optical signal.

3. The method of claim 1 wherein the signal comprises an acoustic signal.

4. The method of claim 1 further comprising:
computing a plurality of magnitudes for respective ones of a plurality of subsets of the transmittances;
computing a plurality of ratios of respective pairs of the plurality of magnitudes; and
comparing the plurality of ratios to a threshold to determine the phase-change pressure for the fluid.

5. The method of claim 4 further comprising selecting the threshold based on a standard deviation computed from the plurality of ratios.

6. The method of claim 1 further comprising:
measuring a plurality of temperatures of the fluid at respective ones of the plurality of pressures; and
confirming the phase-change pressure based on the plurality of temperatures.

7. The method of claim 1 further comprising:
measuring a plurality of depressurization rates at respective ones of the plurality of pressures; and
confirming the phase-change pressure based on the plurality of depressurization rates.

8. The method of claim 1 further comprising:
measuring a plurality of densities of the fluid at respective ones of the plurality of pressures; and
confirming the phase-change pressure based on the plurality of densities.

9. The method of claim 1 further comprising:
measuring a plurality of viscosities of the fluid at respective ones of the plurality of pressures; and
confirming the phase-change pressure based on the plurality of viscosities.

10. The method of claim 1 further comprising:
computing a gas/oil ratio of the fluid; and
when the gas/oil ratio does not exceed a gas/oil ratio threshold and a ratio of the first and second transmittance is an initial ratio of transmittances exceeding the threshold, determining an asphaltene onset pressure for the fluid based on the ratio;
measuring a plurality of temperatures of the fluid at respective ones of the plurality of pressures;
confirming the asphaltene onset pressure based on the plurality of temperatures;
measuring a plurality of depressurization rates at respective ones of the plurality of pressures; and
confirming the phase asphaltene onset pressure based on the plurality of depressurization rates.

11. The method of claim 1 further comprising:
measuring a plurality of depressurization rates at respective ones of the plurality of pressures;
measuring a plurality of temperatures at respective ones of the plurality of pressures and determining whether the phase-change pressure corresponds to a bubble point pressure or a dew point pressure based on the plurality of the plurality of depressurization rates and the plurality of temperatures.

12. An apparatus, comprising a formation fluid analysis tool having:
a flowline;
a valve configured to capture a fluid in the flowline;
a pressure control unit configured to pressurize the fluid at a plurality of pressures;
a scattering detector configured to measure a plurality of transmittances of a signal by the fluid at respective ones of the plurality of pressures; and
a processor configured to compute a first magnitude of a first subset of the plurality of transmittances, compute a second magnitude of a second subset of the plurality of transmittances, compare the first and second magnitudes to determine a phase-change pressure for the fluid.

13. The apparatus of claim 12 further comprising a temperature sensor configured to measure a plurality of temperatures of the fluid at respective ones of the plurality of pressures, wherein the processor is configured to confirm the phase-change pressure based on the plurality of temperatures.

14. The apparatus of claim 12 further comprising a fluid density sensor configured to measure a plurality of densities of the fluid at respective ones of the plurality of pressures, wherein the processor is configured to confirm the phase-change pressure based on the plurality of densities.

15. The apparatus of claim 12 further comprising a fluid viscosity sensor configured to measure a plurality of viscosities of the fluid at respective ones of the plurality of pressures, wherein the processor is configured to confirm the phase-change pressure based on the plurality of viscosities.

16. The apparatus of claim 12 wherein the scattering detector comprises a photo-detector and the signal comprises an optical signal.

17. A method, comprising:
capturing a downhole fluid sample with a downhole tool positioned in a wellbore extending into a subterranean formation;
detecting in-situ a first pressure at which asphaltene particulates begin to precipitate in the downhole fluid sample while depressurizing the downhole fluid sample;
detecting in-situ a second pressure at which gas bubbles begin to emerge from the downhole fluid sample while depressurizing the downhole fluid sample; and
measuring a plurality of temperatures of the downhole fluid sample at respective ones of a plurality of pressures during the depressurization, and confirming the first pressure based on the plurality of temperature.

18. A method, comprising:
capturing a downhole fluid sample with a downhole tool positioned in a wellbore extending into a subterranean formation;
detecting in-situ a first pressure at which asphaltene particulates begin to precipitate in the downhole fluid sample while depressurizing the downhole fluid sample;
detecting in-situ a second pressure at which gas bubbles begin to emerge from the downhole fluid sample while depressurizing the downhole fluid sample; and
measuring a plurality of depressurization rates at respective ones of a plurality of pressures during the depressurization, and confirming the second pressure based on the plurality of depressurization rates.

19. A method, comprising:
capturing a downhole fluid sample with a downhole tool positioned in a wellbore extending into a subterranean formation;
detecting in-situ a first pressure at which asphaltene particulates begin to precipitate in the downhole fluid sample while depressurizing the downhole fluid sample;
detecting in-situ a second pressure at which gas bubbles begin to emerge from the downhole fluid sample while depressurizing the downhole fluid sample; and
wherein the method does not comprise measuring the colloidal instability index of the downhole fluid sample.

* * * * *